(12) United States Patent
Gross et al.

(10) Patent No.: US 8,404,469 B2
(45) Date of Patent: Mar. 26, 2013

(54) EMBEDDED ENZYMES IN POLYMERS TO REGULATE THEIR DEGRADATION RATE

(75) Inventors: Richard A. Gross, Plainview, NY (US); Rachna Dave, Tamil Nadu (IN); Arthur Martin, Horseheads, NY (US); Manoj Genesh, Brooklyn, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 919 days.

(21) Appl. No.: 12/187,949

(22) Filed: Aug. 7, 2008

(65) Prior Publication Data

US 2009/0162337 A1   Jun. 25, 2009

Related U.S. Application Data

(60) Provisional application No. 60/954,472, filed on Aug. 7, 2007.

(51) Int. Cl.
*A61K 38/46* (2006.01)
*C12N 11/00* (2006.01)
*C12N 11/08* (2006.01)
*C12N 9/00* (2006.01)
*C12N 9/02* (2006.01)
*C12N 1/20* (2006.01)
*C12N 15/00* (2006.01)
*C07H 21/04* (2006.01)

(52) U.S. Cl. ....... 435/174; 424/94.6; 435/180; 435/183; 435/189; 435/252.3; 435/320.1

(58) Field of Classification Search .................. None
See application file for complete search history.

(56) References Cited

PUBLICATIONS

Kumar et al. Biomacromolecules. 2000 Spring;1(1):133-8.*
Ness et al. Microspheres, Microcapsules and Liposomes (2003), 6, 199-234.*
Sen et al. Appl Biochem Biotechnol. Dec. 2007;143(3):212-23.*
Chica et al. Curr Opin Biotechnol. Aug. 2005;16(4):378-84.*

* cited by examiner

*Primary Examiner* — Christian Fronda
(74) *Attorney, Agent, or Firm* — Laurence P. Colton; Smith Risley Tempel Santos LLC

(57) ABSTRACT

A biodegradable material, capable of carrying a bioactive agent, comprising a polymer matrix and an enzyme capable of degrading the polymer matrix to enable the release of the bioactive agent.

21 Claims, 34 Drawing Sheets

US 8,404,469 B2

EMBEDDED ENZYMES IN POLYMERS TO REGULATE THEIR DEGRADATION RATE

STATEMENT OF RELATED APPLICATIONS

This application is based on and claims the benefit of U.S. Provisional Patent Application No. 60/954,472 having a filing date of 7 Aug. 2007.

BACKGROUND OF THE INVENTION

1. Technical Field

This invention relates to nanoparticulates, microparticulates, films and other shaped polymer drug delivery systems. More particularly, this invention relates to biodegradable materials, capable of carrying a bioactive agent, comprising a polymer matrix and an enzyme capable of degrading the polymer matrix to release or aid in the release of the bioactive agent from the polymer matrix.

2. Related Art

Biodegradable polymers with a wide range of physical properties and lifetimes have been proposed for a variety of delivery vehicles for various bioactive agents such as drugs, nutraceuticals, growth factors, genes, and other products of biotechnology. Such polymers have a drug encapsulated in a polymeric matrix formulation for the subsequent sustained release of the drug.

Additionally, attaching enzymes to polymer matrices has been explored as a method to endow materials with unique functional attributes. For example, by plasma induced graft copolymerization of acrylic acid, glucose oxidase was conjugated to materials such as polyethylene in order to measure free glucose concentrations in solution. Various oxidative enzymes, such as horseradish peroxidase, glucose oxidase, and lactate oxidase have been incorporated into polyacrylamide-based redox polymers and evaluated for detection of analytes (including glucose and lactate) by "wiring" the enzyme to the redox polymer.

Further, there has been extensive work performed by others to increase enzyme solubility in organic solvents. Solubilization of enzymes in organic media has been primarily for the purpose of performing biocatalysis in homogeneous reaction media. One mechanism by which proteins from an aqueous phase were transferred to the organic phase is by using ionic surfactants. Interactions occur between the surface charges of proteins and the charged head-group of surfactants creating hydrophobic protein-surfactant complexes that can be extracted into organic media. Enzymes containing polymeric coatings, films and plastics have already been synthesized by hydrophobic ion-pairing.

Accordingly, there is always a need for an improved carrier material that can provide increased control of degradation rate for materials. It is to this need, among others, that this invention is directed.

BRIEF SUMMARY OF THE INVENTION

Briefly, the invention is (a) a method of embedding enzymes into materials so as to control or otherwise affect the degradation rate of the material or the ability of the material to degrade, and (b) materials comprising the embedded enzyme. A representative illustrative embodiment of this invention includes an enzyme-embedded material comprising a polymer matrix and an enzyme capable of degrading the polymer matrix. Enzyme-polymer matrix pairs are selected on the basis of that the enzyme(s) are active in the degradation of the polymer matrix.

A representative illustrative method of the invention for preparing an enzyme-embedded material includes the steps of:
(a) selecting a polymer;
(b) selecting an enzyme capable of degrading the polymer;
(c) incorporating the enzyme selected to degrade the polymer into the polymer; and
(d) incorporating a bioactive agent into the polymer.

Another representative illustrative embodiment of this invention includes the incorporation of an active component or encapsulant into the enzyme-polymer matrix. The amount of the active component or encapsulant, such as for example but not limited to a bioactive agent, which is incorporated into the products of the present invention may be such so as to provide or deliver an effective amount, such as a pharmaceutically effective amount or a nutraceutically effective amount, of the active component at its intended location. The degradation of the polymer matrix delivers the active component or encapsulant. Active components that may be encapsulated or embedded in the polymer matrixes include pharmaceutical compositions or compounds, nutraceutical compositions or compounds, nutritional components, biologically active components, flavorants, fragrances, detergents, cosmetics, or surface-active compositions.

These and other aspects of the invention will become apparent from the following description of preferred embodiments taken in conjunction with the included figures. As would be obvious to one skilled in the art, many variations and modifications of the invention may be effected without departing from the spirit and scope of the novel concepts of the disclosure.

BRIEF DESCRIPTION OF THE FIGURES

The various figures contained in this specification illustrate the invention, methods for carrying out the invention, and the properties of the invention, and are included for illustrative purposes and to assist in disclosing the invention.

DETAILED DESCRIPTION OF EMBODIMENTS OF THE INVENTION

Figure 1A:
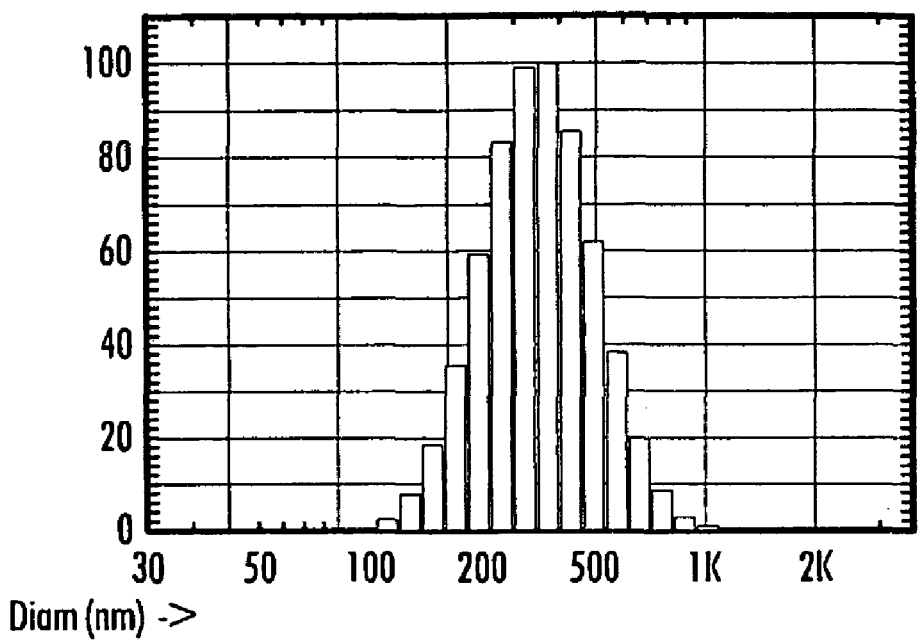
FIG. 1 are intensity-weighted Gaussian Analysis displays with FIG. 1A displaying PCL with active CALB (NS578) with mean diameter of 365.6±130.1 nm and FIG. 1B displaying PCL with deactivated CALB (control) with a mean diameter of 406.8±257.5.

Embodiments of this invention include enzyme-embedded materials comprising a polymer matrix and an enzyme capable of degrading the polymer matrix. Enzyme-polymer matrix pairs are selected on the basis of that the enzyme(s) are active in the degradation of the polymer matrix. In one embodiment, the enzyme and the polymer matrix can be selected so that the enzyme can digest the polymer matrix, which allows for the release of an active agent contained in the matrix. In one example, the polymer matrix constructed from poly(ε-caprolactone) and the enzyme is a lipase, so the lipase can digest the polymer. For example, one such polymer-enzyme combination showing suitable properties is *Candida antartica* Lipase B (referred to herein as CALB) and poly(ε-caprolactone) (referred to herein as PCL). This combination is illustrative only and can be extrapolated to other combinations, and the present invention is not limited to this or any specific combination.

In another example, the polymer matrix is constructed from a poly(lactic acid) (herein referred to as PLA) stereocopolymer and an enzyme known to degrade poly(lactic acid) such as Proteinase K can be embedded in the matrix. A wide range of polyesters are known that can be used in this invention including poly(butylene succinate), poly(ethylene terephthalate), and poly(dioxanone). Other examples include the use of natural or modified natural polymers as matrix materials. One example is the family of polyhydroxyalkanoates for which polyhydroxyalkanoate depolymerases are well-known and could be embedded in the matrix to control its degradation rate. Polysaccharides (e.g. starch, pullulan, pectin, cellulose, chitosan, chitin, xylan, galactomannans, and xanthan) can be used in their native form or modified by crosslinking or other reactions such as esterification (e.g. acetylation and octanyl succinate derivatives), carboxymethylation, or reactions with epoxides (most commonly ethylene oxide and propylene oxide) can be used as matrix materials. In another example, synthetic polymers that fall within the family of vinyl polymers can be used as matrix materials. Important examples include polyvinyl acetate and poly(methyl acrylate) where the embedded enzyme will degrade the acetate and methyl ester bonds of the respective polymers to from water soluble materials.

The enzyme embedded within the polymer matrix can by selected from a wide range of natural enzymes known to degrade the matrix polymer. Suitable enzymes may be known or can easily be identified by well known screening methods that will be active in degrading the matrix polymers. Furthermore, combinations of enzymes can be used so that one enzyme degrades the bonds formed during polysaccharide modification and another degrades the polysaccharide chain. For example, a cutinase known to degrade ester bonds such as acetate groups from polyvinylacetate can be added along with an enzyme chosen from the family of glycosidase, to modified polysaccharides such as starch acetate, cellulose acetate, and pectin acetate. Cutinases represent one family of enzymes that can be used to degrade acetate and methyl ester bonds of polyvinyl acetate and poly(methyl acrylate), respectively.

Factors that control the rate at which the polymeric material degrades include the concentration of the enzyme in the material, the enzyme kinetics with respect to polymer degradation, the enzyme kinetics with respect to the polymer can be dependant on the polymer matrix, the polymer shape (e.g. changing the shape may affect the rate of substrate transport into and out of the material), the environment in which the enzyme embedded polymer is to be subjected to (e.g. the environment can vary in temperature, pH, ionicity and other factors that alter enzyme activity), the fluid dynamics of the outer environment (e.g. fluid dynamics can alter the rate at which substrates, products and the enzyme itself is removed from the enzyme-embedded material environment). Other factors that also can alter the rate of polymer degradation are readily available to those with ordinary skill in the art. By embedding an enzyme in the material and by taking into account these factors, among others, the rate of material degradation can be accelerated so that material degradation matches that for the required application.

Further, degradation of the enzyme-embedded material can be triggered by placing the material in an aqueous environment, e.g., if the enzyme falls under the classification of a hydrolase. Alternatively, the embedded enzyme may have a substance that must be removed prior to its functioning in polymer degradation. For example, a photoactivated trigger can be attached to the enzyme so that, when irradiated at the appropriate wavelength, the photoactivated group will release from the enzyme rendering the enzyme active to function in degradation of the polymer matrix. In addition, the enzyme may lack a substance such as a co-factor that must be provided so that the enzyme can function in polymer degradation. Once the enzyme is activated it can then function to degrade the polymeric material.

In addition to the polymers listed above, polymers that can be used with this embodiment include polymers that can use the availability of an enzyme that is active for its degradation. Other examples of polymers that can be used include aliphatic polyesters, natural or modified polysaccharides, aliphatic polycarbonates, polyamides including oligopeptides, pseudopoly (amino acids), peptides of higher molecular weight, protein-based materials, polymers prepared from fatty acids with degradable linkages, polyurethanes built from polyols that contain degradable units such as ester groups, and mixed linkage polymers that contain various fractions of the above polymer building blocks.

The enzymes can be introduced into materials by many routes. For example, enzymes can be dispersed with polymers by using enzymes in their free-powder form and simply dispersing them within the polymer matrix by physical mixing. Enzymes may be first modified to increase their miscibility with polymers by, but not limited to, coupling with fatty acids, polyethylene glycol, and by forming associations between enzymes and surfactants, which is often known as ion or surfactant pairing. Such modified enzymes can then be dispersed with the polymer by mixing in the melt or in a common solvent that dissolves both enzyme and polymer. An alternative way to include enzymes within polymers is by mixing emulsions where the polymer can be in either the continuous or dispersed phase. In one example, the polymer may be in the continuous phase where the enzyme is in the dispersed phase. Upon removal of solvents the enzyme becomes dispersed in the polymer where the size of droplets determines the size of enzyme aggregates within materials. Enzymes may exist in polymers where they are completely dissociated from each other or enzymes may to various extents be associated with each other as aggregates of various size.

In one embodiment, enzyme-embedded material synthesis provides a relatively straightforward mechanism for the incorporation of bioactive agents within the polymer composite material. More particularly, as the polymer is being synthesized, hydrolytic enzymes become associated with polymers that are being formed and are thereby incorporated within the matrix. Enzyme incorporated within the matrix may leach from an immobilization support into the product formed. An example is the synthesis of polyesters by either condensation or ring-opening polymerizations where the catalyst used consists of an enzyme physically immobilized on a matrix material. During the polymerization, the enzyme can leach from the support and become physically or chemically associated with the polymer. Simultaneously, bioactive materials to be released from the polymer-enzyme matrix can be incorporated within the polymerization reaction. Physical entanglements and favorable hydrophobic interactions can be used to facilitate retention of bioactive agents in the absence of covalent linkage.

Enzyme-embedded materials may be in various shapes as needed for the application. Examples include microparticles, nanoparticles, fibers, films, highly porous materials, and/or scaffolds for tissue engineering.

In one example, the embedded polymer has medical applications in the embodiment of a slowly degrading polymer that can retain its shape and material performance to provide the time needed for a wound healing repair. The current invention allows the use of such materials as the embedded enzyme remains inactive as long as a substance that surrounds or is attached to an enzyme site remains in place, or a substance such as a cofactor is not available to the enzyme. However, once healing is completed or it is deemed the appropriate time for the polymer to degrade, the enzyme is activated and degradation begins. Degradation of the polymer material by the embedded enzyme may be used to enable release of a bioactive substance in wound healing, to effect tissue repair, to provide factors that control cell differentiation, to provide signals for growth of specific cell types, and more.

In another example, sutures constructed from an enzyme embedded material can remain intact for a period of time based on the enzyme degradation rate. Enzymes may be embedded in suture fibers to regulate the fiber degradation rate. This concept can also be used for tissue engineering where the matrix degradation rate is controlled by the activity of the embedded enzyme. Embedded enzyme materials may be incorporated into transdermal patches to control the release of active agents. Polymers for bone repair such as screws and bone plates can be constructed of materials with enzymes embedded. This can provide such materials with the advantage of maintaining their shape and strength until the bone is healed and, subsequently, the screw(s) and bone plate can be degraded at the desired rate.

Bulk degrading materials (e.g. PLA) can rapidly lose their strength and begin to fragment into microcrystalline substances that then remain in the body for times beyond their use. If these materials were constructed with an embedded enzyme, the fragments could be degraded more rapidly at a time where they are no longer useful.

Alternative applications for enzyme-embedded products can be in cosmetic and agricultural applications. Enzyme-embedded materials can be used to release active ingredients to the skin at a rate determined by the enzyme-polymer matrix selected. Furthermore, enzyme activity can be triggered by light, substances on the skin, changes in temperature and other physical and chemical phenomena. The same concepts can be applied to the release of agricultural materials such as herbicides and soil nutrients. Alternatively, enzyme-embedded materials can be used as agricultural mulch materials that can degrade when desired instead of at a rate determined by factors such as the amount of light to which the material is exposed.

In another embodiment, the enzymes are embedded at specific locations within the matrix including, but not limited to, a material surface or a coating applied to the surface. The enzyme can be used for the controlled degradation of the surface, thus releasing substances such as antibacterial or antifungal compounds. Alternatively, degradation of the surface catalyzed by embedded enzymes can be used to clean a surface.

In another embodiment, a method for preparing an enzyme-embedded material includes the steps of:
  (a) selecting a polymer;
  (b) selecting an enzyme capable of degrading the polymer;
  (c) incorporating the enzyme selected to degrade the polymer into the polymer; and
  (d) incorporating a bioactive agent into the polymer.

The amount of the active component or encapsulant that is incorporated into the products of the present invention, such as but not limited to a bioactive agent, may be such so as to provide or deliver an effective amount, such as a pharmaceutically effective amount or a nutraceutically effective amount, of the active component at its intended location. Active components that may be encapsulated or embedded in the polymer matrixes include pharmaceutical compositions or compounds, nutraceutical compositions or compounds, nutritional components, biologically active components, flavorants, fragrances, detergents, cosmetics, or surface-active compositions.

The pharmaceutical compounds or compositions and biologically active compositions may, for example, include antibiotics, analgesics, vaccines, anti-inflammatory agents, antidepressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, steroids, compositions to promote growth such as hormones, or other growth stimulating agents, mixtures thereof, and the like.

Nutraceutical components may, for example, include components that promote health or prevent disease or enhance well-being, such as antioxidants, phytochemicals, hormones; vitamins such as Vitamins A, B1, B2, B6, B12, C, D, E, and K; pantothenate; folic acid; pro-vitamins; minerals such as calcium, selenium, magnesium salts, available iron, and iron salts; microorganisms such as bacteria, live lactobacilli, fungi, and yeast; prebiotics; probiotics; trace elements; essential and/or highly unsaturated fatty acids such as omega-3 fatty acids and mid-chain triglycerides; nutritional supplements; enzymes such as amylases, proteases, lipases, pectinases, cellulases, hemicellulases, pentosanases, xylanases, and phytases; pigments; oligopeptides; dipeptides; and amino acids; and mixtures thereof.

Biologically active components that may be encapsulated may, for example, include agriculturally useful compositions to either prevent infestation such as herbicides, pesticides, insecticides, rodenticides, fungicides, mixtures thereof, and the like or to promote growth such as hormones, fertilizers, or other growth stimulating agents.

EXAMPLE 1

The results obtained from these studies demonstrated that CALB can be successfully encapsulated in nanoparticles of PCL using water-in-oil-in-water double emulsion evaporation technique. More particularly, a self-degrading system was developed by encapsulating fluorescently labeled CALB in nanoparticles of PCL. CALB was covalently linked by reaction of the iso-thiocyanate group of the fluorescein 5-isothiocyanate with the amine group of the CALB at basic conditions and room temperature. The nanoparticles were successfully processed by the (w/o/w) double emulsion evaporation technique with enzyme encapsulation efficiency of 9% for both active and de-actived enzyme loaded nanoparticles. Dynamic light scattering confirmed nanoparticles sizes of 365.6±130.1 with activated CALB and 406.8±257.5 for de-activated lipase as controls. In vitro release studies resulted in a nine-fold increase in cumulative release of the fluorescently tagged CALB over the control that contained irreversibly inhibited CALB. Moreover, LC-MS analysis of supernatant removed at time intervals resulted in a 20-fold increase in hydroxyl-hexanoic acid degradation products for active CALB loaded PCL nanoparticles when compared to inhibited CALB loaded nanoparticles. Examination of the morphology and structural integrity of nanoparticles using scanning electron microscopy (SEM) confirmed significant degradation after 576 hours for PCL nanoparticles with active CALB. Control PCL nanoparticles were rather smooth and intact which means they maintained their structural integrity during the same incubation period.

1. Material and Methods
  a. Materials:
  Fluorescein 5-isothiocyanate was purchased from Molecular Probes and stored at −20° C. before use. Poly(vinylalcohol) 89% hydrolyzed molecular weight 13,000-23,000, sodium bicarbonate, ammonium bicarbonate and ammonium sulphate were all purchased from Sigma-Aldrich. CALB from *Candida antartica* (NS578) was received as a gift from Novozyme and used as received. Dimethylsulfoxide was purchased Aldrich Chemical Co. and Paraoxon-ethyl and nickel affinity matrix were purchased from Sigma.

b. Irreversible Inhibition of CALB (NS578) with (Paraoxon-ethyl) O,O-Diethyl O(-4-nitrophenyl) Phosphate for Encapsulation Controls:
  The CALB (NS578) present in 10 mg/ml concentration was irreversibly inhibited by mixing 2 ml with 40 µl (0.18 mmol.) of paraoxon-ethyl. The loss of activity was measured by using p-nitrophenylbutyrate substrate. Ultraviolet Spectroscopy with absorption at 405 nm revealed total inhibition of CALB.

c. Procedure for Conjugation of CALB with Fluorescein 5-isothiocyanate:
  In a 20 ml scintillation vial 50 mg of CALB (NS578) was dissolved in 5 ml of 0.1 M sodium bicarbonate buffer pH 9.0 to give a final concentration of 10 mg/ml. In a separate centrifuge tube 5.0 ml of FITC DMSO dye solution was prepared from 10 mg/ml of fluorescein 5-isothiocyanate from Molecular Probes. The 5 ml of lipase solution in sodium bicarbonate was then mixed with 3.6 ml of fluorescein 5-isothiocyanate solution and mildly agitated for 1 hour at room temperature. The conjugated lipase was purified by dialysis against 0.1 M ammonium bicarbonate buffer by ultra-centrifuging for 90 minutes against buffer using a MacroSep 10 K Omega centrifugal filter (Pall Corporation) at 5000 g at 4° C. The inhibited lipase was also conjugated using the same procedure described above.

d. Determination of Degree of Labeling:
Protein concentration (CALB)=0.583−[2.64×0.3)]×100/90, 461=0.004512 M where $\epsilon$ for CALB is 90,461 $cm^{-1}M^{-1}$.
To calculate the degree of labeling for CALB:
FITC per CALB molecule=$A_{494}$×dilution factor/68,000×protein concentration, where 68,000 $cm^{-1}M^{-1}$ is the molar extinction coefficient of the dye at pH 8.0 at 494 nm. Since 2.64×100/68,000×0.0045=0.8589, therefore there are 0.8589 moles of FITC per mole of CALB.

e. Procedure for Characterization of the Morphology of PCL Nanoparticles:
The surface morphology (roundness, smoothness, and formation of aggregates) and the size of the nanoparticle formulations were studied by scanning electron microscopy (SEM). The PCL nanoparticles for SEM analysis were prepared by finely spreading onto metal stubs then coating with platinum in a Fisons Polaron sputter coater and observed by SEM using a Hitachi S-530 with an accelerating voltage of 25 kv.

f. Procedure for Particle Size Determination:
Particle size of PCL nanoparticles was determined by a NICOMP 370 DLS Particle Sizing Systems, Inc., from Santa Barbara, Calif. Nanoparticles prepared by double emulsion were appropriately diluted with double-distilled water. Light from a laser (5 me HeNe) is focused into a cuvette containing the prepared dulute suspension of nanoparticles.

g. Procedure for In Vitro Release Studies:
In triplicates 20 mg of PCL nanoparticles were added to 50 ml Beckman centrifuge tubes and 20 ml of Tris-HCl buffer, pH 8.0, 20 mM was added. The nanoparticle suspensions were continuously stirred in a thermoshaker (50 rpm) at 37° C. At preselected time intervals, samples were collected and centrifuged at 16,500 rpm for 20 minutes. The samples were reconstituted with fresh Tris-HCl buffer.

h. Determination of Protein Content in Nanoparticles:
The amount of FITC-lipase was determined by the hydrolysis technique. To a 20 ml scintillation vial, 20 mg of the loaded-nanoparticles were incubated in 5 ml of 0.1 N NaOH containing 5% (w/v) sodium dodecyl sulphate (SDS) at room temperature until complete dissolution of the nanoparticles. The solution was filtered with a 0.1 μm membrane filter (Pall Corporation) and assayed by UV spectroscopy.

Figure 1B:
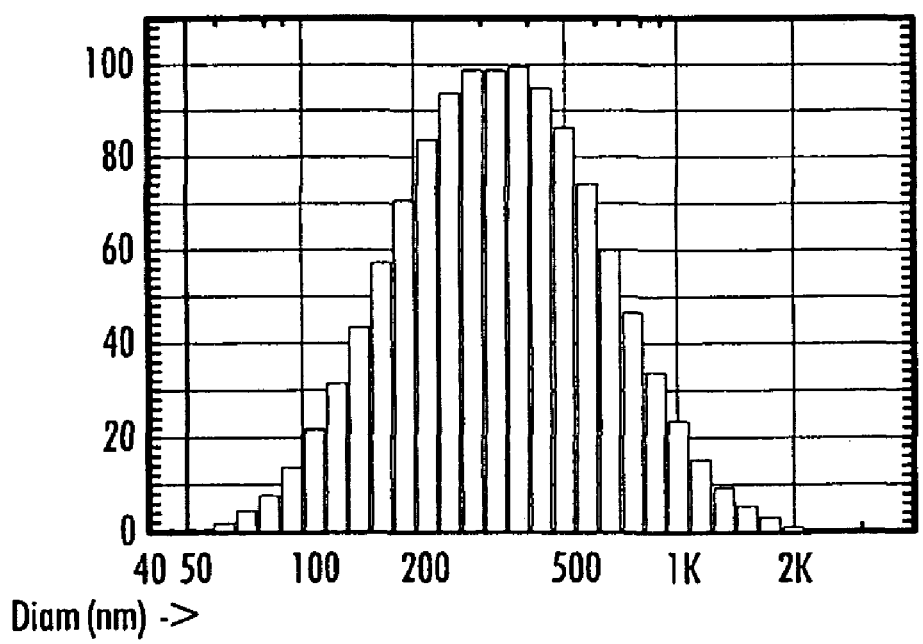
Figure 2:
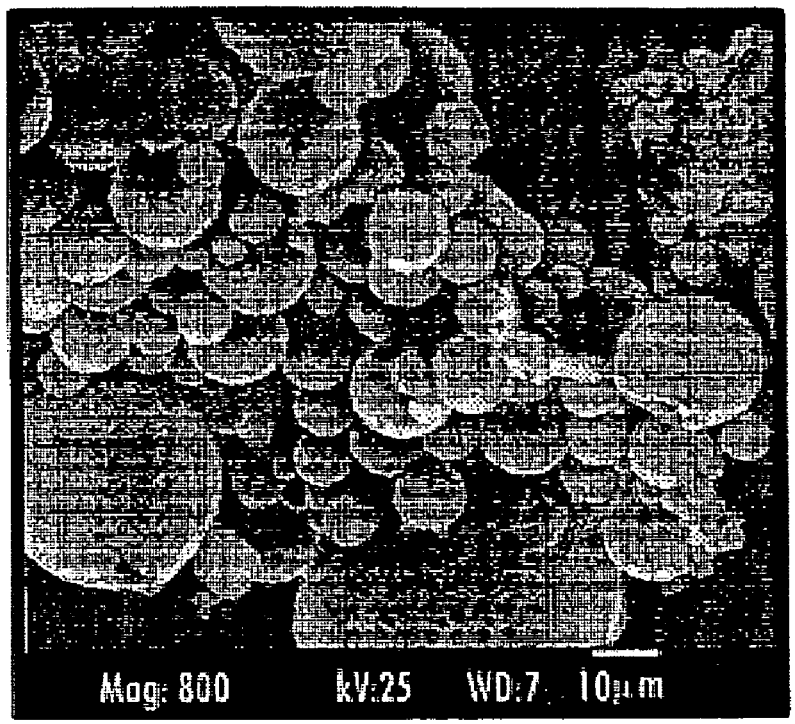
FIG. 2 is an SEM of PCL nano-particles containing active CALB at 0 hrs.
Figure 3:
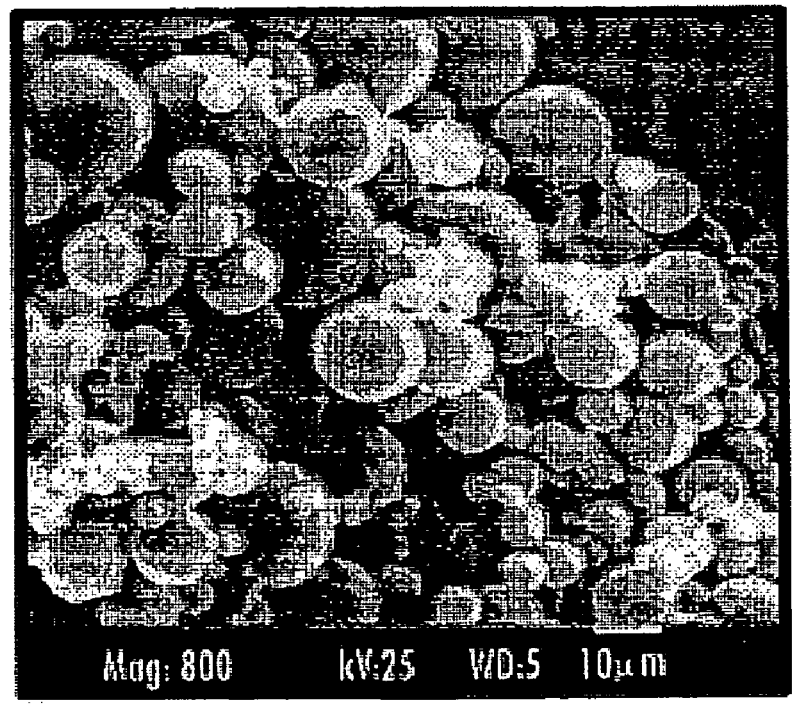
FIG. 3 is an SEM of PCL nano-particles containing de-activated CALB after 0 h of incubation.
Figure 4:
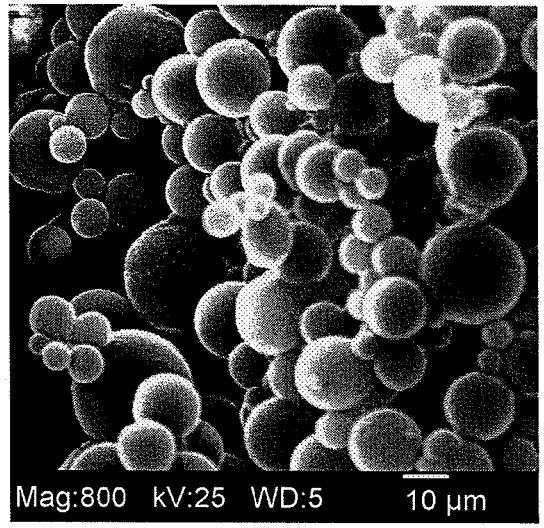
FIG. 4 is an SEM of PCL control nanoparticles with de-activated CALB after 576 h of incubation showing nanoparticles that maintained their original appearance having smooth surface and spherical shape.
Figure 5:
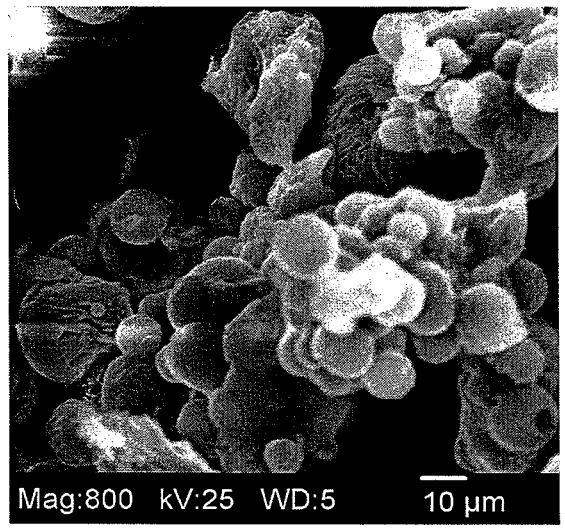
FIG. 5 is an SEM of PCL with active CALB (NS576) nanoparticles after 576 h of incubation showing nanoparticles that were ruptured and perforated, with striated surfaces.
Figure 6:
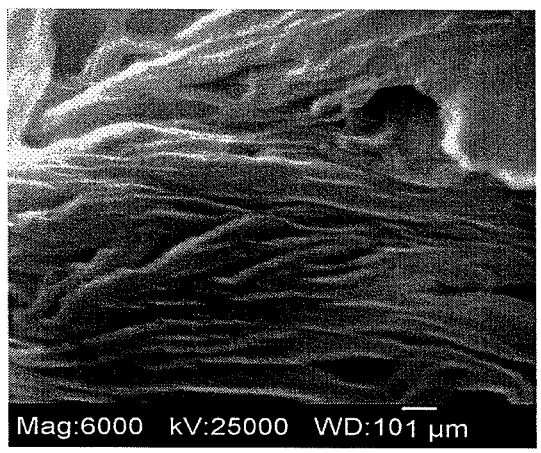
FIG. 6 is an SEM of PCL with active CALB (NS576) nanoparticles showing striated regions that may be associated with residual crystalline regions in enzyme-degraded nanoparticles were observed.
Figure 7:
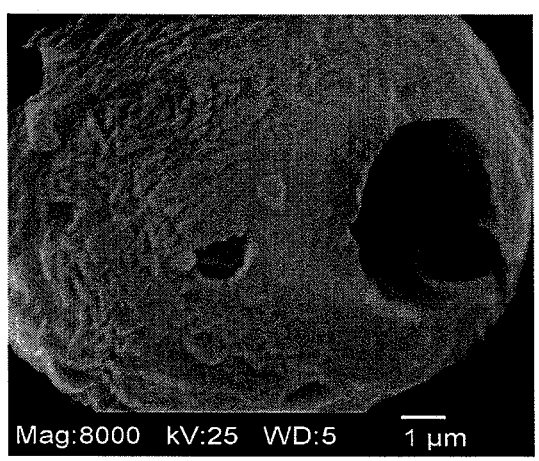
FIG. 7 is an SEM of PCL with active CALB (NS576) nanoparticles showing that incubations of nanoparticle resulted in perforations or large holes.
Figure 8:
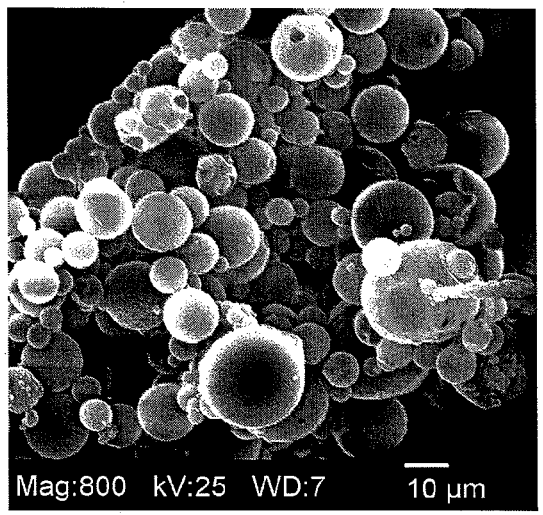
FIG. 8 is an SEM of PCL control (deactivated enzyme) after 576 h of incubation showing nanoparticles that are smooth and remained intact.
Figure 9:
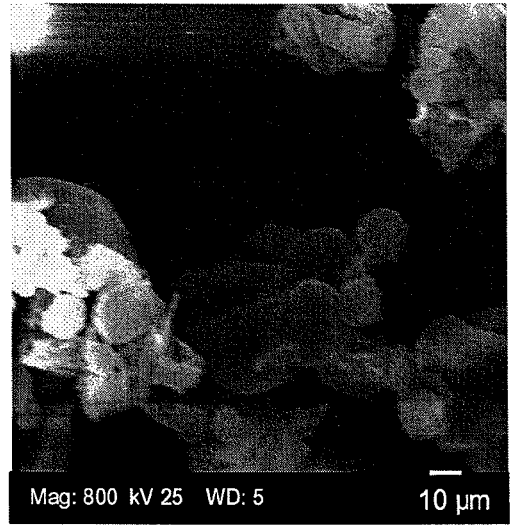
FIG. 9 is an SEM of PCL with active CALB (NS576) nanoparticles after 576 h of incubation showing remaining particles that appear aggregated and particle shape has dramatically changed.
Figure 10:
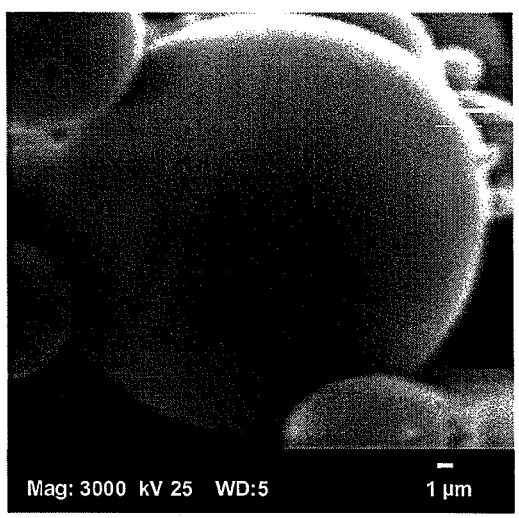
FIG. 10 is an SEM of PCL with deactivated enzyme after 576 h of incubation showing nanoparticles that maintained their original spherical shape with smooth surfaces.
Figure 11:
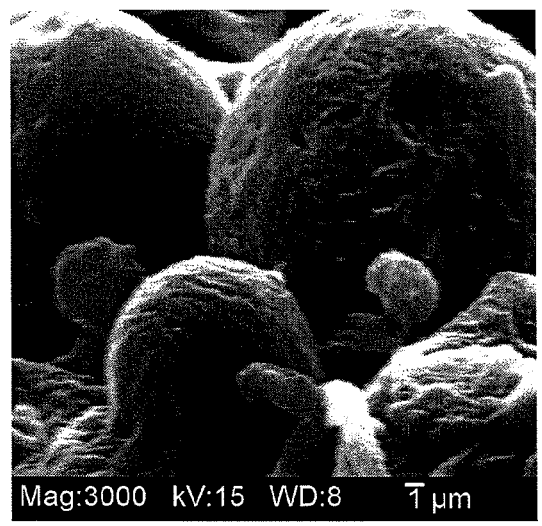
FIG. 11 is an SEM of PCL with active CALB (NS576) nanoparticles after 576 h of incubation showing nanoparticles that were ruptured and perforated, with striated surfaces.
Figure 12:
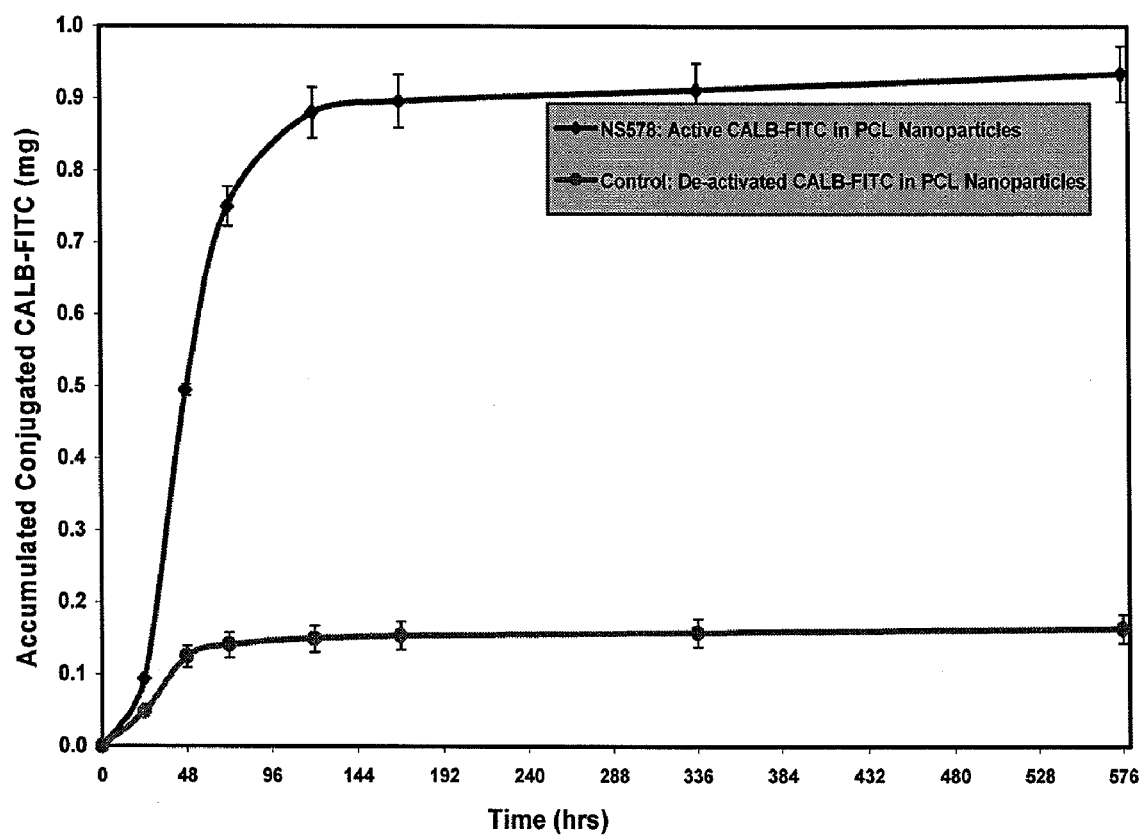
FIG. 12 show release profiles for poly(ε-caprolactone) nanoparticles loaded with active CALB-FITC and de-activated CALB-FITC in which studies were conducted for 576 h in 20 mM Tris-HCl buffer pH 8.0 at 37° C. and buffer was removed every 24 h for fluorescent measurements and reconstituted with fresh buffer.
Figure 13:
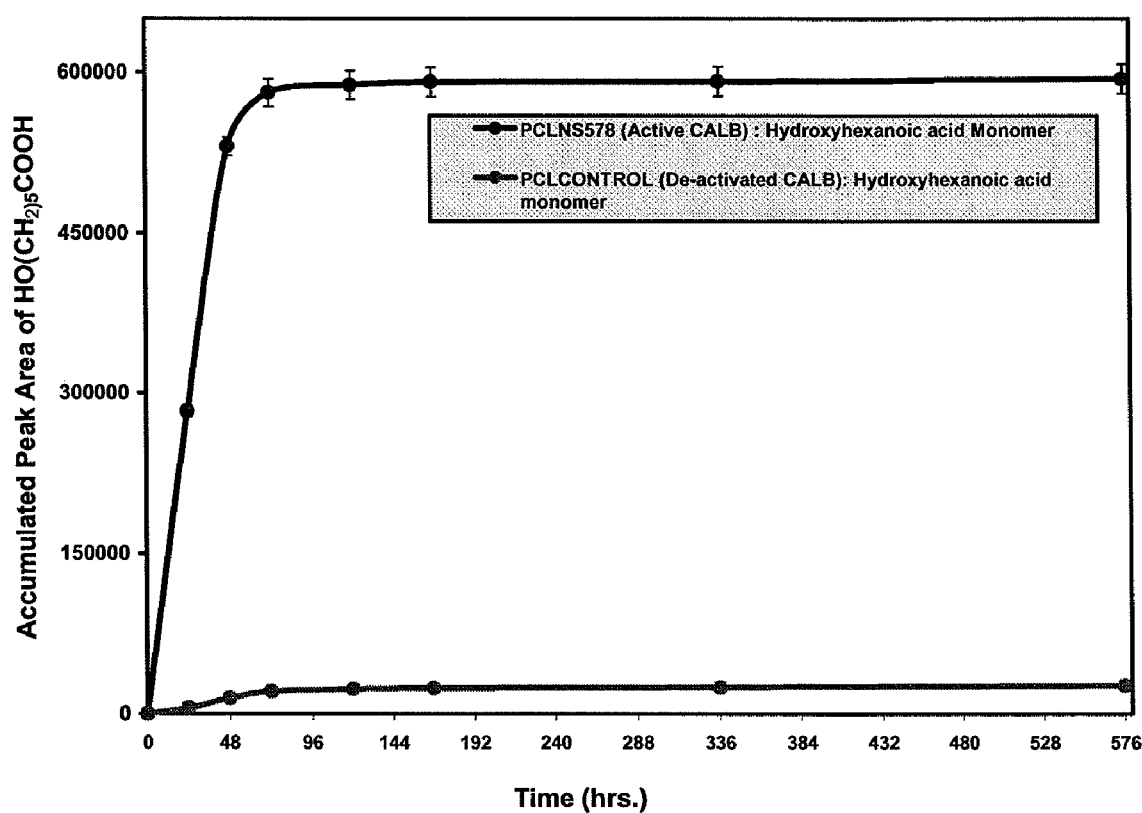
FIG. 13 shows displays LC-MS analysis of water soluble hydroxyhexanoic acid degradation products form PCL nanoparticles loaded with active CALB and de-activated CALB as control in which the release study was carried out for 576 h in TRIS-HCl buffer 20 mM, pH 8.0 at 37° C.

2. Results a. Particle Size Analysis:
The size distribution of PCL nanoparticles loaded with CALB-FITC was assessed by photon correlation spectroscopy (NICOMP 370 DLS instrument) using Intensity-Weighted Gaussian distribution analysis to represent the mean diameter particle size. Two different PCL formulations were prepared, one with active CALB-FITC and the other with inhibited CALB-FITC to establish controls for release studies. The results in FIGS. 1A and 1B show that PCL nanoparticles, entrapped with both active and de-activated CALB, have similar size distribution. The particle size of PCL nanoparticles with active enzyme is 356±130.1 nm while, for the in-active control, PCL nanoparticles were 406±257.5 nm.

b. Morphology of Nanoparticles Characterized by SEM:
The morphology and size distribution can be visualized in FIGS. 2-11. The nanoparticles have a smooth surface for both active and non-active lipase loaded nanoparticles characterized directly after freeze drying (FIGS. 2 and 3). However, significant structural damage can be seen for nanoparticles loaded with active CALB-FITC after 576 hours of incubation, as can be seen in the figures. In contrast, the control de-activated CALB-FITC loaded nanoparticles had a smooth spherical surface and maintained their overall structural integrity after 576 hours of incubation. More specifically, FIGS. 2 and 3 show SEM of PCL samples at 0 h; FIGS. 4 and 5 show SEM of PCL samples incubated for 576 h (Sample Set 1); FIGS. 6 and 7 show SEM of PCL samples loaded with active CALB after incubation for 576 h, mMagnified: 8000×; and FIGS. 8 through 11 show SEM of PCL samples incubated for 576 h (Sample Set 2).

c. Fluorescently Labeled CALB Encapsulated in PCL Nanoparticles:
Active CALB loaded PCL nanoparticles demonstrated pronounced release profiles with a nine-fold increase over inhibited CALB loaded nanoparticles. This result is in accordance with the scanning electron microscopy visuals which show striated and ruptured morphology for nanoparticles after 576 hours (FIG. 6). Hence, the active lipase is readily degrading PCL used as the matrix. The highest degree of release takes place in the first 48 h and then reaches a plateau where little or an inconsequential amount of protein release is observed. Of importance is the Tris-HCl buffer that was removed and reconstituted with fresh buffer at all time intervals studied in FIG. 12. Hence, protein released into the medium was removed regularly so that, the degradation observed is attributed to matrix hydrolysis catalyzed by CALB entrapped within or residing at nanoparticle surfaces.

d. LC-MS of PCL Loaded Nanoparticles:
The degradation profiles for PCL nanoparticles containing active CALB-FITC demonstrated a 20-fold increase in the degradation product hydoxy-hexanoic acid relative to incubations with the inhibited CALB-FITC loaded nanoparticles. Analysis of the degradation profile in FIG. 13 shows that the degradation occurs rapidly during 48 h. Subsequently, the degradation slowed and beyond 72 h little or further degradation occurred. The large difference in degradation products formed by the control and active CALB-loaded PCL nanoparticles demonstrated by LC-MS, along with protein release data and SEM analyses confirmed that, by embedding CALB within PCL nanoparticles, large increases in matrix decomposition and release of encapsulated substances can be achieved.

The PCL nanoparticles loaded with active and non-active CALB had similar loading efficiency of about 9%, which is a typical loading capacity for hydrophilic biomolecules using the double emulsion evaporation technique. Particle size characterization of PCL loaded nanoparticles with active CALB-FITC revealed a size of 365.6±130.1 nm. For the control, where CALB was deactivated by reaction with nitrophenylphosphate inhibitor, its size was 406.8±257.5 (FIGS. 1A and 1B).

EXAMPLE 2

This example shows that embedding enzymes within polymeric matrices with activity in polymer hydrolysis can be used to 'tune' polymer bioresorption kinetics. In this example, PCL was selected because of its slow bioresorption rate which limits its general use for medical applications such as in tissue engineering scaffolds and as matrices for drug encapsulation. CALB was selected as the enzyme catalyst for polymer hydrolysis. CALB was solubilized in isooctane by pairing with the anionic surfactant sodium bis(2-ethylhexyl) sulphosuccinate, AOT. Once this was accomplished, surfactant paired CALB and PCL were dissolved into a common solvent and films were cast. The ratio of AOT-CALB to PCL in films was varied and its effect on film hydrolytic degradability was studied. Confocal microscopy was used to analyze the uniformity of CALB distribution within PCL films.

Figure 14:
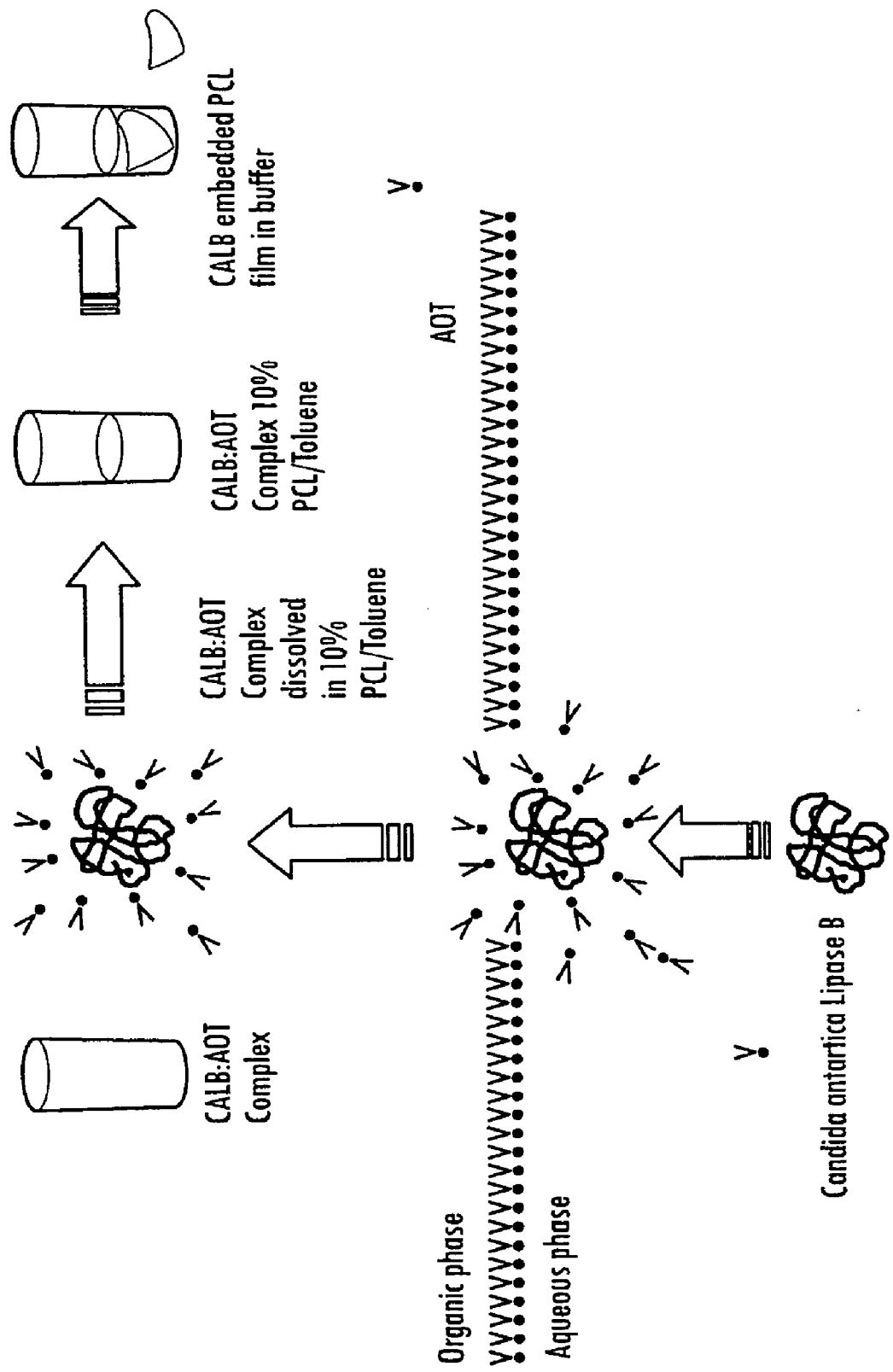
FIG. 14 shows an illustrative scheme of the present invention illustrating CALB extraction into isooctane and embedding CALB:AOT complex in PCL film.

1. Methods and Materials a. Materials:

CALB in the form of a spay dried powder was a gift of Novozymes (Bagsvaerd, Denmark). The SDS-PAGE analysis of an aqueous solution of this powder showed a single band with a molecular weight (33 K Da) corresponding to CALB. Aerosol OT [sodium bis (2-ethylhexyl) sulfosuccinate], isooctane (2,2,4-trimethylpentane), toluene, FluoroTag™ FITC-Conjugation Kit and doxorubicin hydrochloride were purchased from Sigma Chemical, St. Louis Mo. PCL, P-787 ($M_w$ 80 000), was obtained from Dow Chemical Company (USA). Micro BCA™ Protein Assay Kit was obtained from Pierce. All purchased reagents and chemicals were obtained in the highest available purity and were used as received. In all cases, water used was deionized (DI).

b. Preparation of Ion-Paired CALB:

CALB was extracted from its aqueous solution into isooctane by forming an ion-paired complex with sodium bis(2-ethylhexyl)sulfosuccinate (AOT) (see FIG. 14). The optimal pH for lipase recovery is 4.5 and the optimal $CaCl_2$ concentration is 9 mmol $dm^{-3}$. Shaking at 100 rpm was the most efficient mode of extraction avoiding aggregation of CALB-surfactant complexes.

c. CALB Extraction in Isooctane:

In a typical extraction procedure, an aqueous 20 mM sodium acetate buffer solution (200 mL, pH 4.5) was prepared that contained 9 mM calcium chloride, 0.25% v/v isopropanol, and 100 mg of CALB. To this solution an equal volume of 2 mM AOT/isooctane was added and the two phases were incubated for 15 min at 30° C. with shaking (100 rpm). Then, the mixture was centrifuged at 3000 rpm (30° C., 10 min) to obtain a clear organic phase. The organic phase was recovered and assayed for protein content by measuring UV absorption of CALB aromatic amino acid residues at 280 nm. The ion-paired lipase (0.17±0.05 g) was obtained in dried form by evaporating the organic solvent by nitrogen purging.

d. Preparation of PCL Films with Embedded Enzyme:

PCL films were prepared by solution casting. PCL (1 g, $M_w$ 80 000) was dissolved in 10 mL toluene and, after complete solubilization, varied amounts of CALB-AOT complex was added. The resulting solution was immediately poured onto a glass plate and films were cast using a film applicator. Toluene was evaporated under vacuum until films reached constant weight (generally overnight). Films were then cut so they were 2 by 2 cm and 100±23 µm thick. Each PCL film with embedded CALB/AOT weighed 35±2 mg.

e. Film Degradation:

In one method, films were placed in glass vials containing 10 mL potassium phosphate buffer solution (25 mM, pH 7.0). Incubations were performed with shaking (200 rpm) at 37° C. Within a time period no greater than 24 h, buffer in glass vials was replaced with fresh buffer. After preselected incubation times, films were removed from the medium, washed with potassium phosphate buffer, and then dried to constant weight.

Also, degradation studies were performed with continuous exchange of vial contents with fresh buffer. This was accomplished by using a home-built system consisting of glass vials fitted with a septum cap through which inlet and outlet glass tubes were inserted. The inlet was connected via tubing to a reservoir containing potassium phosphate buffer (20 mM, pH: 7.0) while the outlet was connected to a vessel where buffer and other materials from incubations in glass vials was collected. Inlet and outlet tubes were connected to a peristaltic pump set to maintain the flow-rate at 1 mL/min. Thus, the liquid content of vials (10 mL) was replaced every 10 min. As above, PCL films with varied quantities of AOT-CALB were placed in glass vials containing 10 mL potassium phosphate buffer (20 mM, pH 7.0). Incubations were performed for predetermined times with shaking (200 rpm) at 37° C. Subsequently, films were removed, washed and dried as above.

f. Drug-Release from Films:

PCL (1 g) and 0.17 g CALB-AOT complex were dissolved in 10 mL toluene. Doxorubicin (0.5 mg) was added and the solution was poured onto a glass plate to prepare films. Films were incubated as above using the method where buffer was replaced at regular intervals. The doxorubicin release profile was determined by LC-MS (see below). Corresponding film degradation was monitored by weight loss.

g. Instrumental Methods:

Confocal Laser Scanning Microscopy (CLSM) studies: CALB was tagged with Fluoroscein Isothiocynate, FITC, using the FluoroTag FITC-Conjugation Kit from Sigma. The FITC-CALB conjugate was then extracted in isooctane as described above. PCL films were then prepared as above except using the FITC-CALB-AOT complex in place of non-labeled CALB-AOT. Films for CLSM studies were mounted on a cover slip and imaged using a 63×1.2 numerical aperture water immersion objective. The 488-nm line from an argon laser was used for excitation and the emission was collected by setting the detection bandwidth between 495 and 525 nm. Images were collected at depths from 0.00 to 48.00 µm.

Molecular weight Determination: Molecular weights were determined by gel permeation chromatography (GPC) using Waters 510 model pump, 717 auto sampler, 2414 refractive index detector, and a PLgel 5 um MIXED-D 300×7.5 mm column (Polymer Labs Ltd.). Chloroform was used as eluent at a flow rate of 1.0 mL/min. Sample concentrations of 2-5 mg/mL and injection volumes of 20-30 µL were used. Eleven narrow polystyrene standards with molecular weights ranging from 900K to 580 (from Polymer Lab Ltd.) were used to calibrate the system. System calibration data and relative molecular weight calculations were acquired and processed by Waters Empower software (with GPC option).

Scanning Electron Microscopy studies: Samples were applied to carbon-coated specimen stubs and coated with 10 nm Au/Pd in an argon field (BalTec MED020, Fohrenweg, Liechtenstein). Images were obtained by field-emission scanning electron microscopy (AMRAY 1910, KLA-Tencor, Bedford, Mass.) at an accelerating potential of 5 kV and working distance of 15 mm.

2. Results

Figure 15:
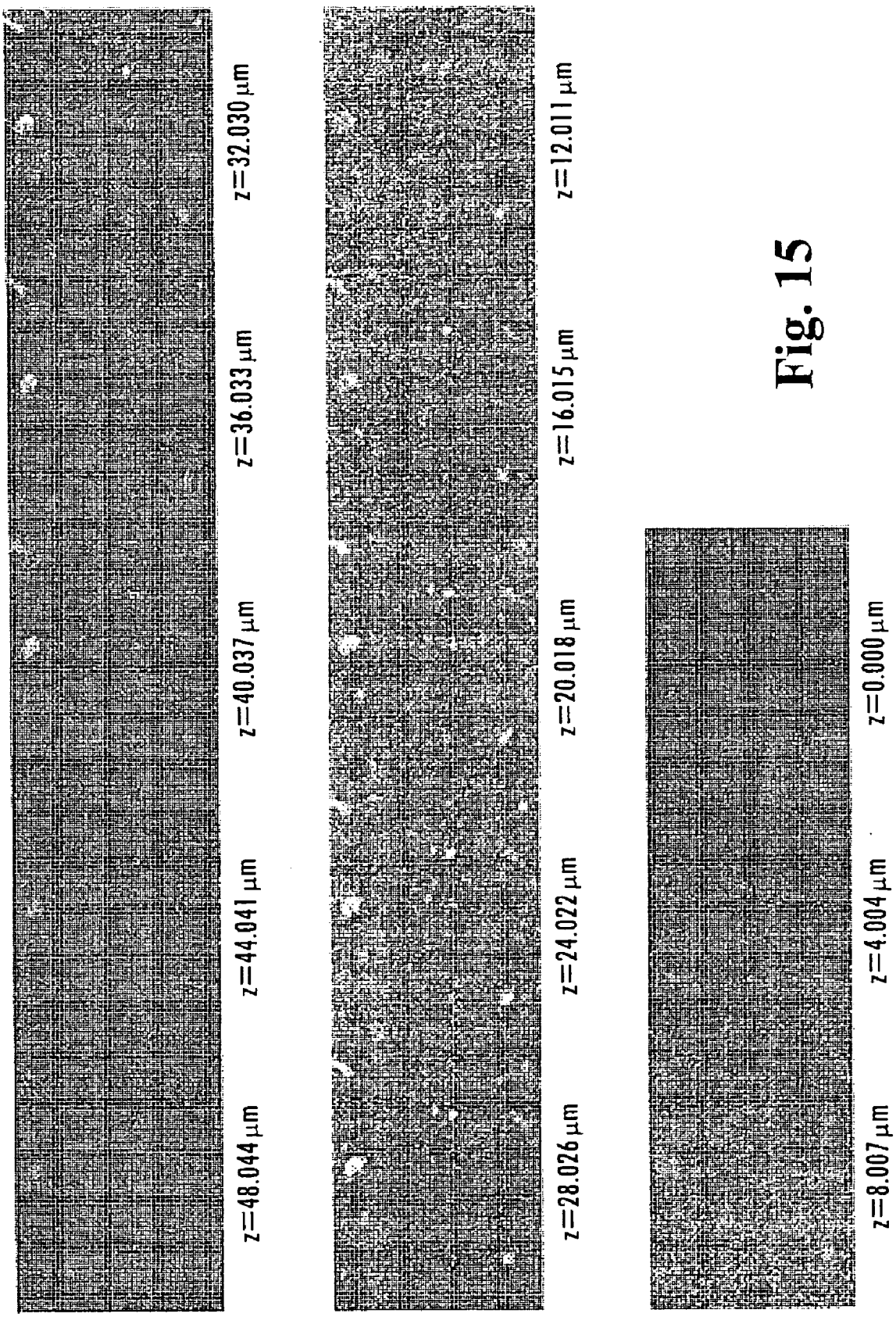
FIG. 15 is a confocal micrograph displaying the average distribution of the FITC-CALB AOT conjugate within a 100 μm thick PCL film, with the figure representing images taken at various depths ranging from 0-48 μm.
Figure 16:
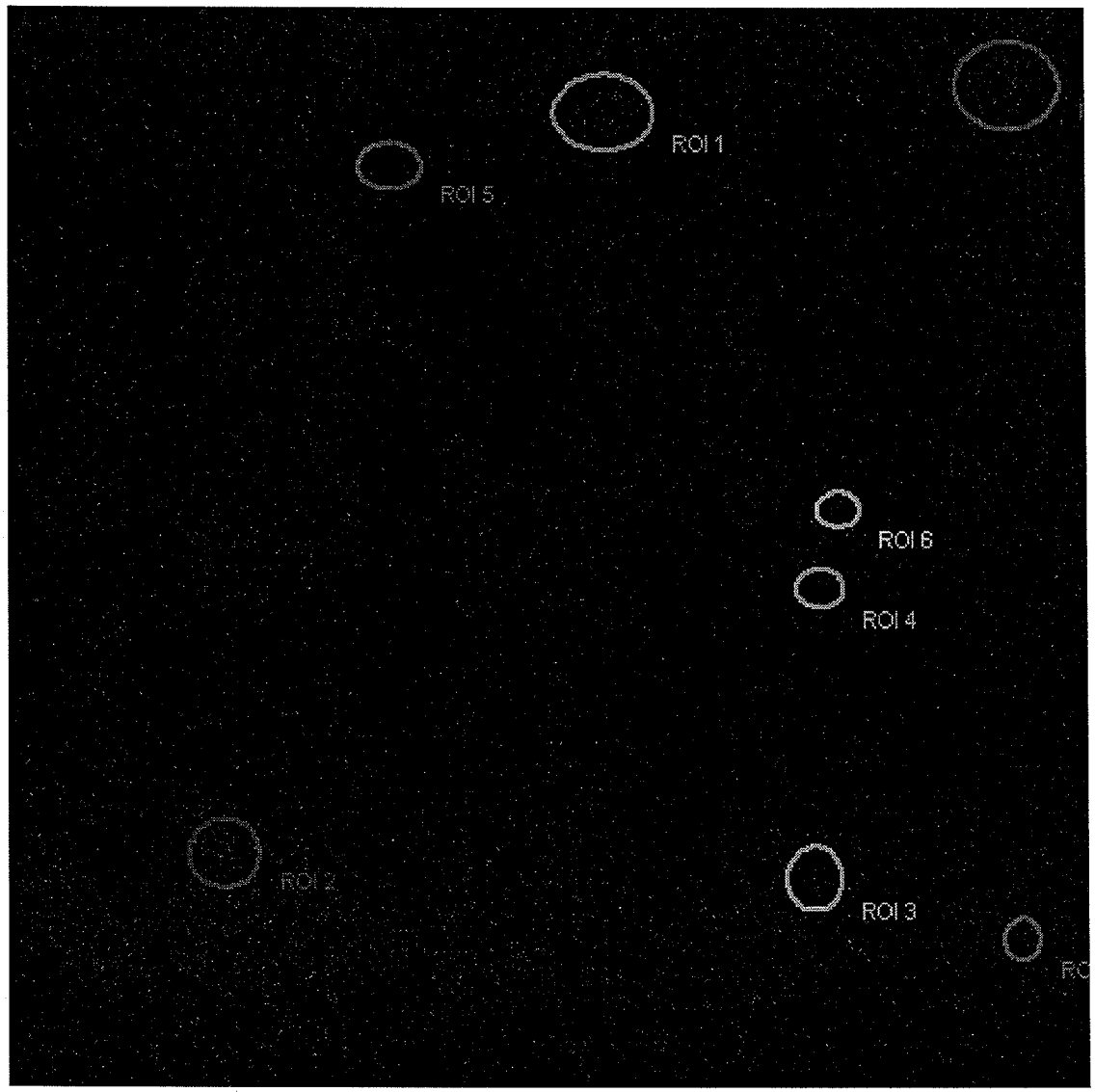
FIG. 16 is a confocal micrograph displaying within circles the fluorescent regions as Regions of Interest (ROI) for which data was generated for intensity versus depth plots shown in FIG. 17.
Figure 17:
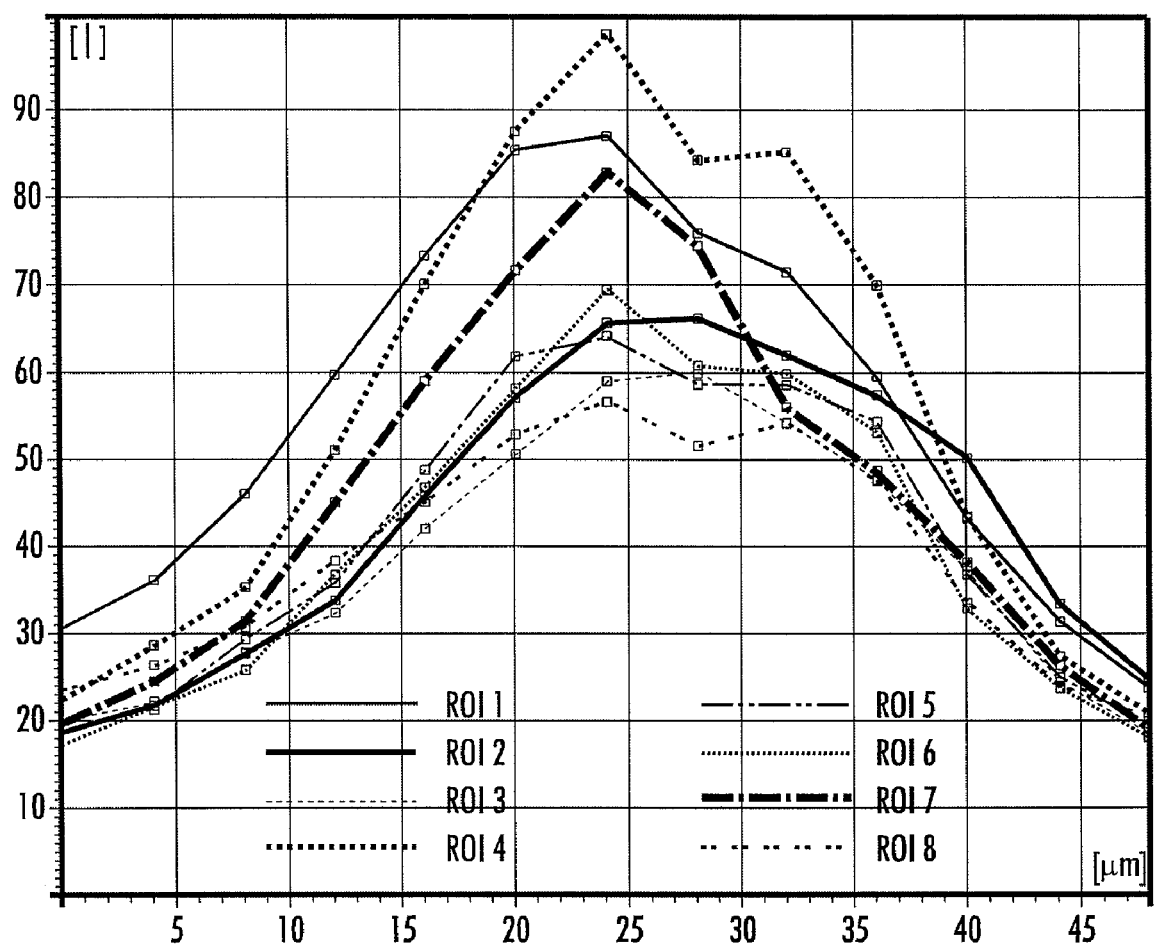
FIG. 17 are intensity versus depth profiles of CALB aggregates in which the aggregates are marked designating the ROI (Region of Interest) observed (see FIG. 16).
Figure 19:
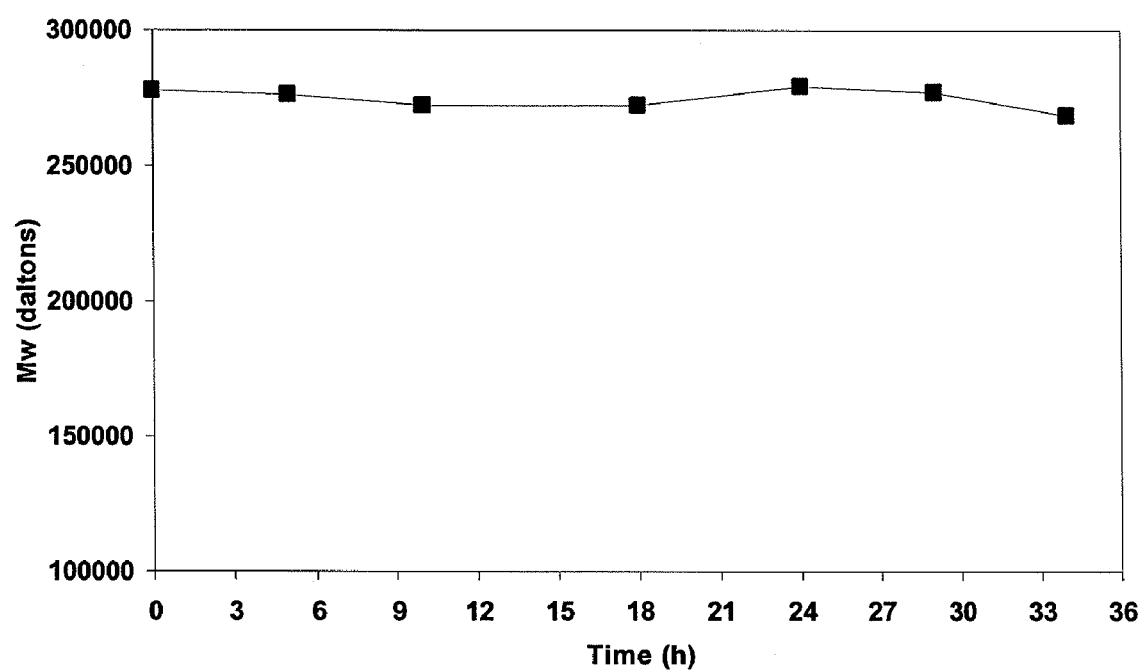
FIG. 19 is a molecular weight analysis, determined by gel permeation chromatography, of recovered PCL films that were embedded with 19.4% w/w CaLB:AOT complex and incubated in buffer in batch-mode degradation studies.
Figure 20A:
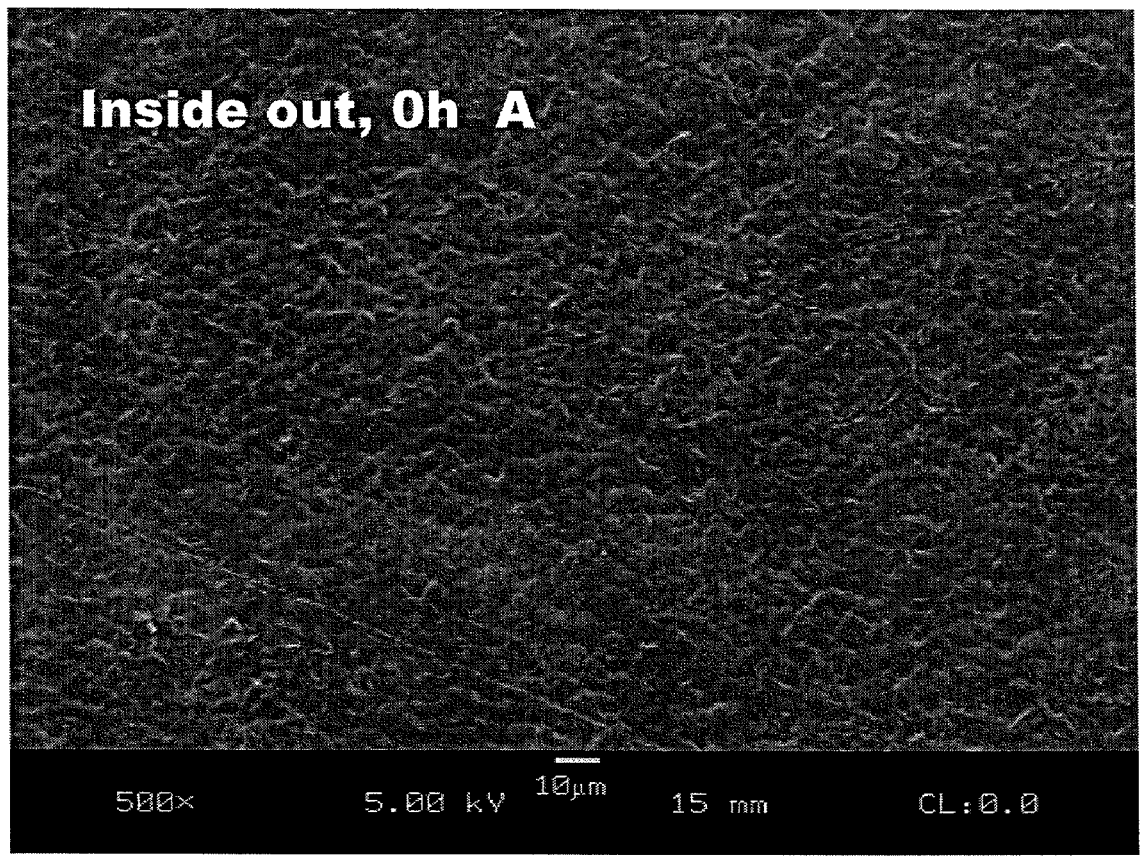
FIG. 20 is a representative SEM micrographs of recovered PCL films that were embedded with 19.4% w/w CALB:AOT complex and then incubated in buffer in the batch mode for 0 h (FIG. 20A), 30 min (FIG. 20B), 2 h (FIG. 20C), 4 h (FIG. 20D), and 6 h (FIG. 20E).
Figure 20B:
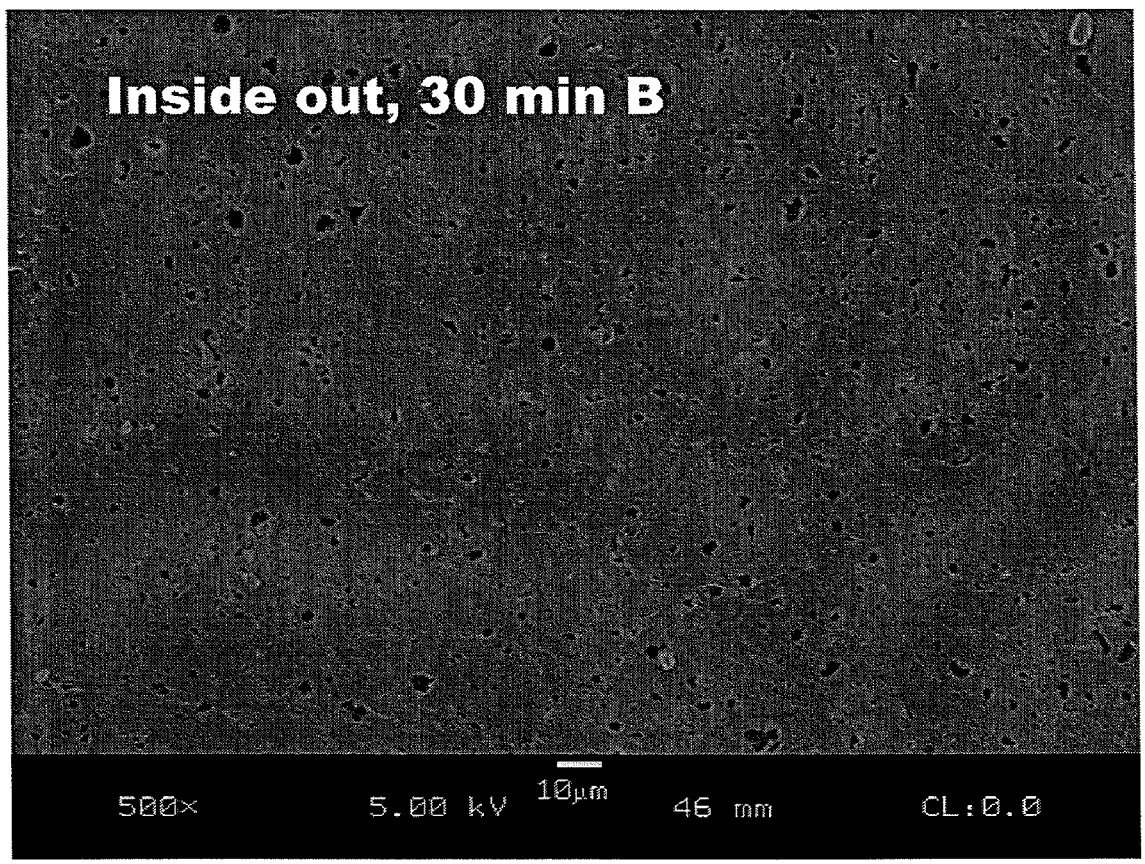
Figure 20C:
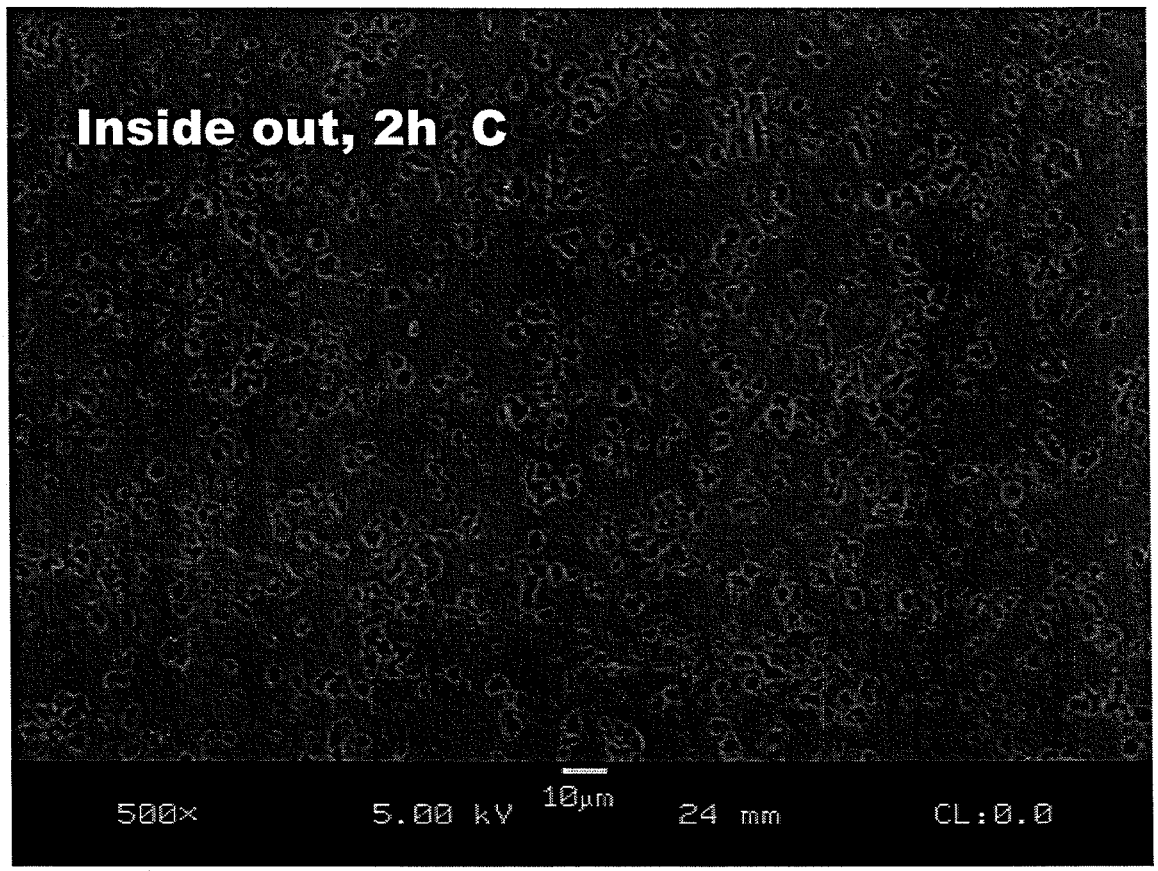
Figure 20D:
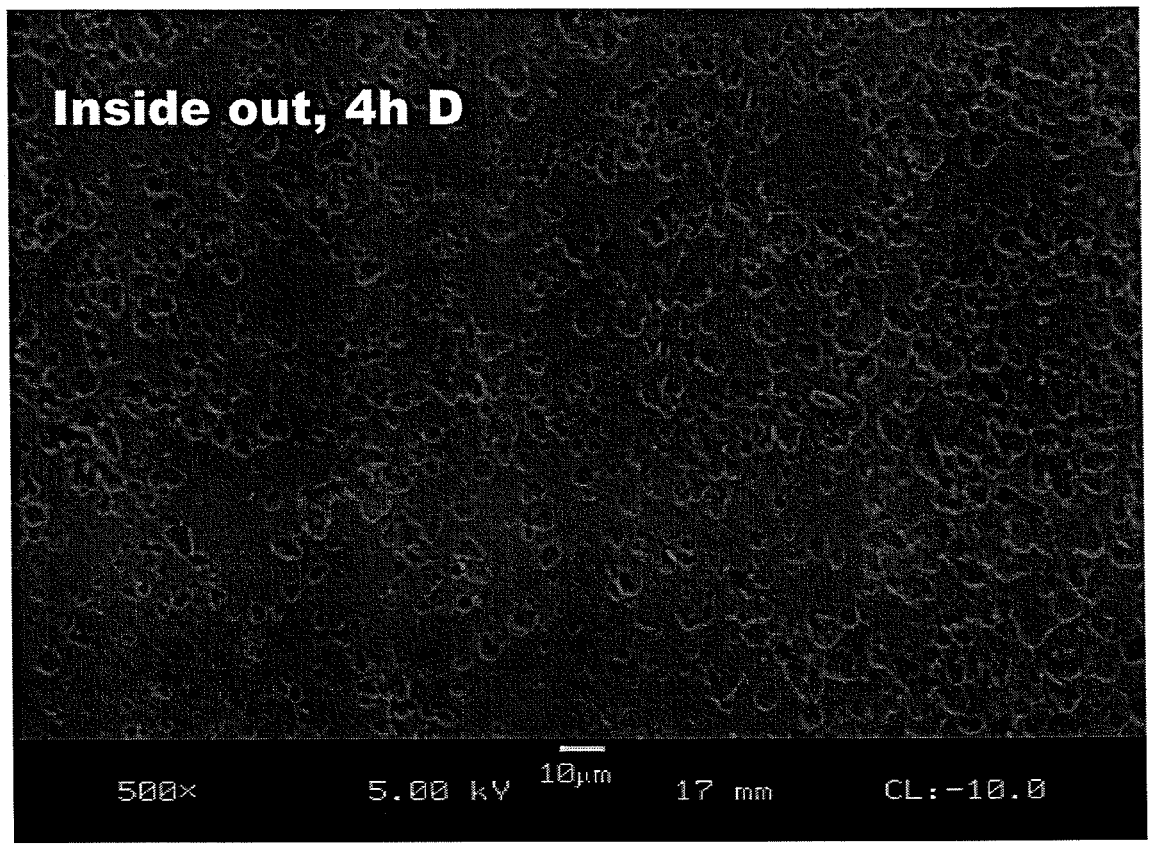
Figure 20E:
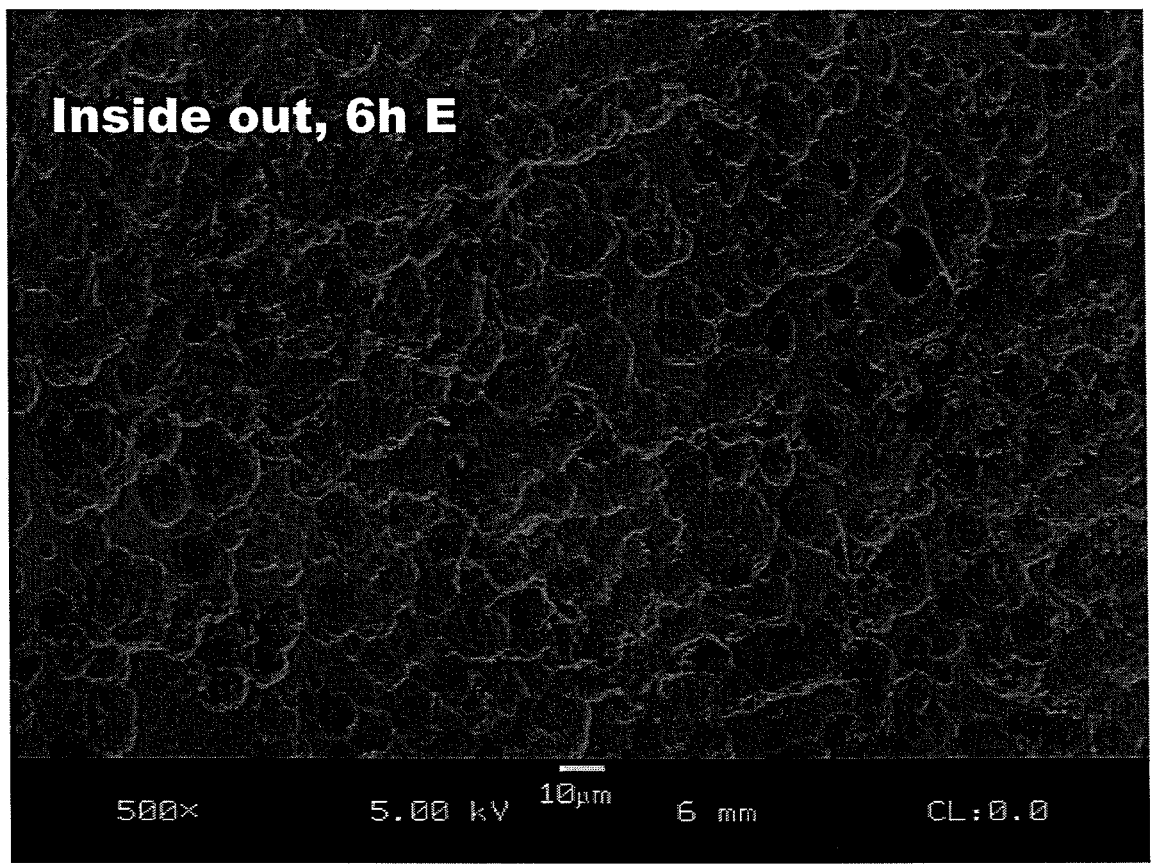
Figure 21A:
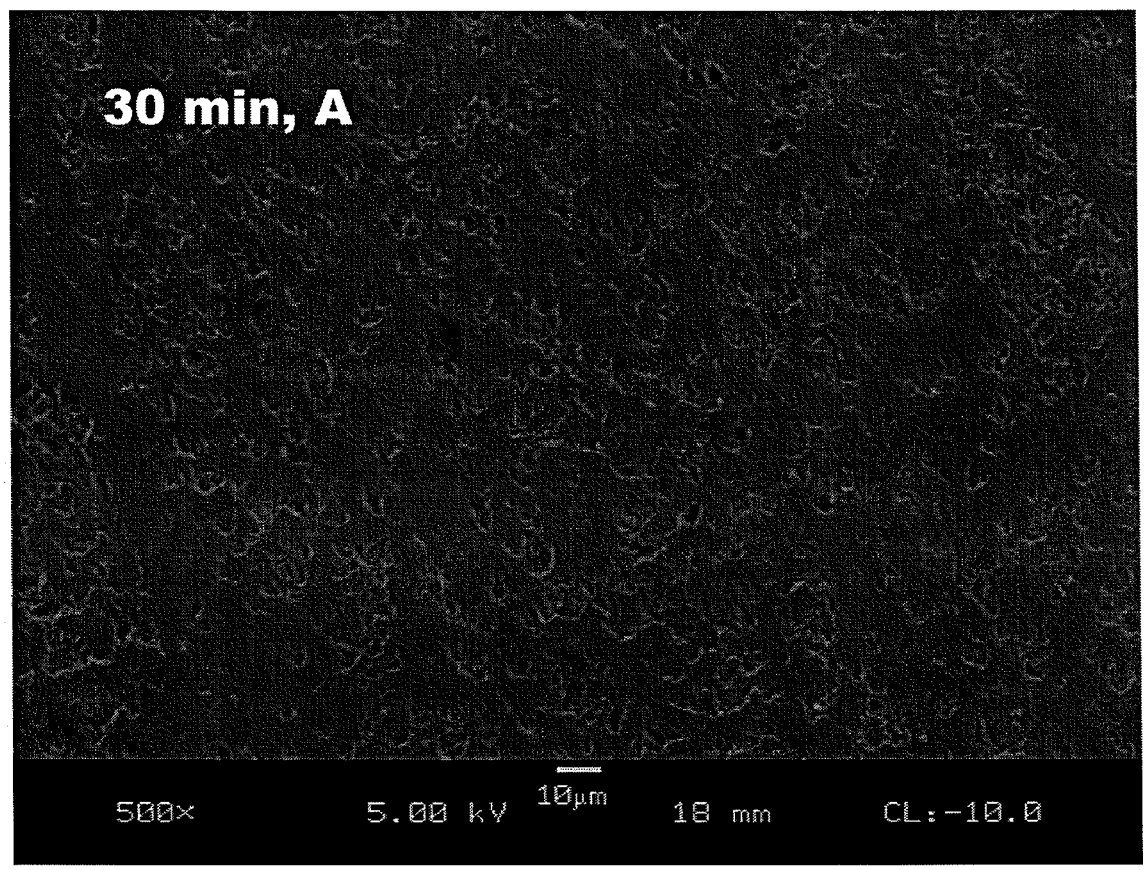
FIG. 21 are representative SEM micrographs of recovered PCL that did not contain embedded enzyme in which an equivalent quantity of CALB used for 19.4% w/w embedded experiments was placed in the incubation medium and the experiments were performed in the batch mode, and in which the SEM pictures are displayed from films recovered after incubation periods of 30 mins (FIG. 21A), 60 min (FIG. 21B), and 4 h (FIG. 21C).
Figure 21B:
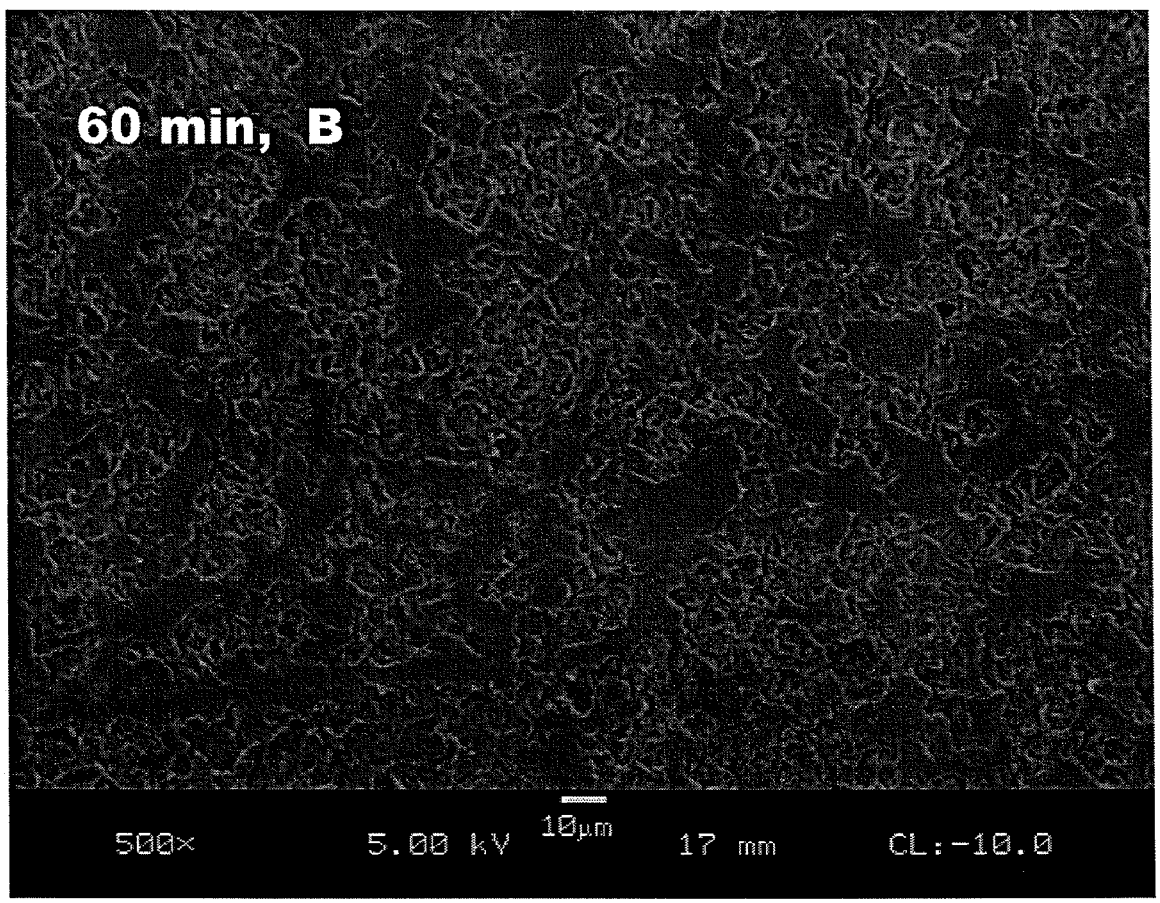
Figure 21C:
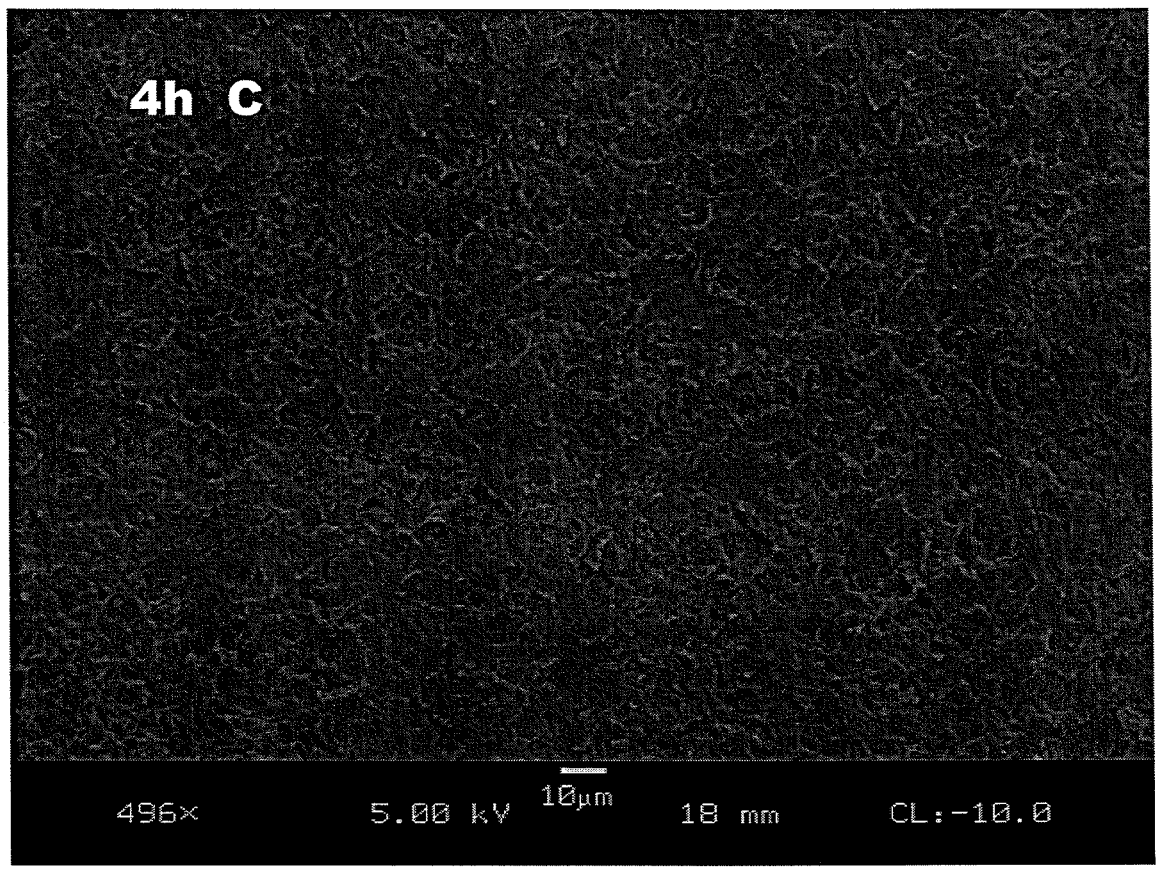

Each of the concentrations of the enzymes disclosed herein can serve as a separate example. By varying the concentration of the enzyme, the lifetime of the film can be controlled. Thus, the exemplary concentrations disclosed herein are for illustrative purpose only.

a. Distribution of CALB in the PCL Films:

Confocal images of 5% w/w FITC-labeled CALB:AOT complex embedded in PCL films were recorded at various depths from 0.00 to 48 µm (FIG. 15). The images show the presence of CALB at each depth. The distribution of CALB is heterogeneous, although it is present throughout the film. To further define CALB distribution as a function of film depth, fluorescent regions showing the presence of aggregates were randomly selected and marked as regions of interest (ROI, FIG. 16). Eight ROIs were selected and for each, a depth vs. intensity profile was plotted. Inspection of these plots in FIG. 17 shows that fluorescence intensity is maximal at depths from 20 to 30 µm. Thus, CALB aggregates formed are found predominantly at an intermediate distance between the center and surface of films.

b. Degradation Studies:

Films consisting of PCL with from 3 to 19.4% CALB:AOT complex were incubated in potassium phosphate buffer solution (25 mM, pH 7.0) at 37° C. with shaking (200 rpm). Buffer in incubations was replaced so that CALB and PCL-degradation products released into the medium would not accumulate. Furthermore, by this approach, for all PCL film incubation studies, the medium pH did not substantially decrease.

c. Results for time course studies of PCL film weight loss as a function of time and CALB:AOT loading is plotted in FIG. 18. PCL films with 19.4%-by-wt CALB-AOT complex degraded most rapidly. With increased incubation time, SEM showed these films became increasingly thinner and were visually observed to be more transparent and fragile. By 24 h film weight loss reached 50% and, by extending the study to 48 h, almost complete transformation of the film to water soluble products occurred. By reducing the content of embedded AOT:CALB complex in PCL films to 5.71%, film degradation slowed dramatically so that 30 d is required for complete film weight loss. In other words, by decreasing the enzyme content by a factor of about 3.4, the degradation time was prolonged by 15 fold. Further decrease in CALB-AOT complex to 3%-by-wt further increased film lifetime. Hence, by varying embedded enzyme concentration from 0 to 19.4%, a series of PCL materials were prepared that had widely variable lifetimes. Without enzyme-embedding, PCL lifetime under similar incubation conditions was over 2-years limiting its utility.

d. Molecular Weight Analysis of the PCL Film During Degradation:

For PCL films containing 19.4% (w/w) CALB:AOT, molecular weight and film weight loss as a function of incubation time are shown in FIG. 19. As film weight loss progressed, PCL molecular weight showed no substantial change. Also, polydispersity ($M_w/M_n$) values remained nearly constant (1.6±0.2). A PCL film containing no enzyme and incubated for 34 h showed no weight loss. These results support that film degradation does not proceed by an accelerated bulk erosion hydrolysis mechanism. Instead, it appears as if enzyme within films creates numerous surfaces from which PCL is degraded. This multiple surface erosion mechanism would leave the molecular weight of bulk PCL, that is beneath multiple new surfaces created by enzyme degradation, unchanged. This degradation mechanism differs from incubation of PCL film with externally added enzyme in that, instead of CALB being restricted to the very outer surface of films, degradation by embedded CALB leads to a dramatic increase in surface area that is available for subsequent degradation.

e. Surface and Cross-Sectional Distribution of CALB in PCL Film:

The enzymatic degradation of PCL films was visualized by recording SEM photomicrographs. SEM photographs recorded at 0 h and after 30 min and 2 h incubations of PCL films containing 19.4% (w/w) AOT-CALB complex are shown in FIGS. 20A, 20B, and 20C, respectively. The surface of films appears uniform prior to incubation in buffer. However, after 2 h, the SEM micrograph shows that films have holes dispersed over a smooth surface (FIG. 20C). After 6 h (FIG. 20E), the film surface has an extensive networks of pits with smaller islands of smooth surface regions. When PCL films was incubated with CALB dissolved in buffer, where the CALB concentration was equal to that in 2 by 2 cm films with embedded 19.4% w/w CALB-AOT (e.g., without embedding enzyme within films), no holes dispersed along the film surface surrounded by large smooth areas were observed after 4 h incubations (FIG. 21C). The degradation profile of these films with enzyme placed in the buffer, not embedded in films, is very rapid when compared with the embedded enzyme films. These films disintegrated completely in 10 h of incubation. Fifty percent weight loss was observed at 5 h of incubation, where as in the embedded film, 50% weight loss was seen at 24 h of incubation.

Figure 22A:
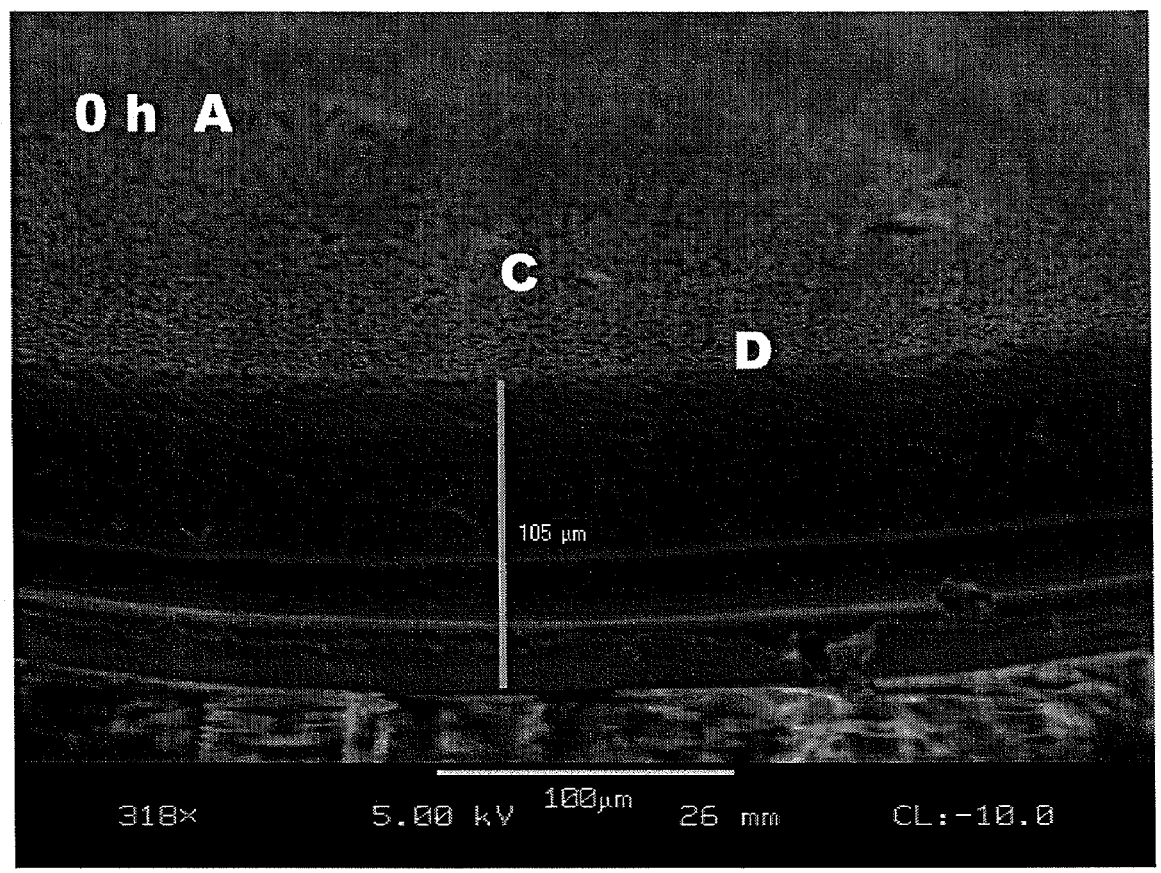
FIG. 22 are representative SEM micrographs of recovered PCL recorded of film cross-sections at 71° in which PCL films were embedded with 19.4% w/w CALB:AOT complex and then incubated in buffer in the batch mode for 0 h (FIG. 22A), 2 h (FIG. 22B), 4 h (FIG. 22C), 6 h (FIG. 22D), and 1 h (FIG. 22E).
Figure 22B:
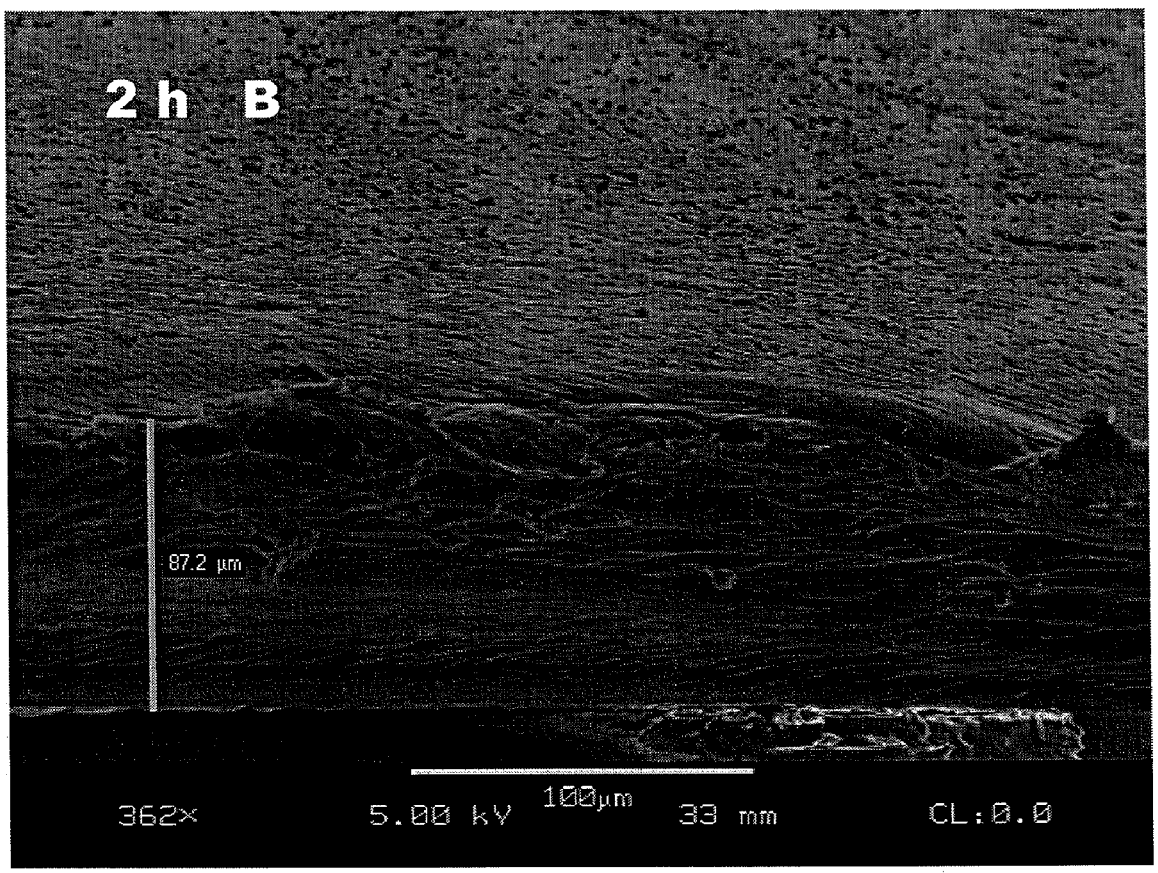
Figure 22C:
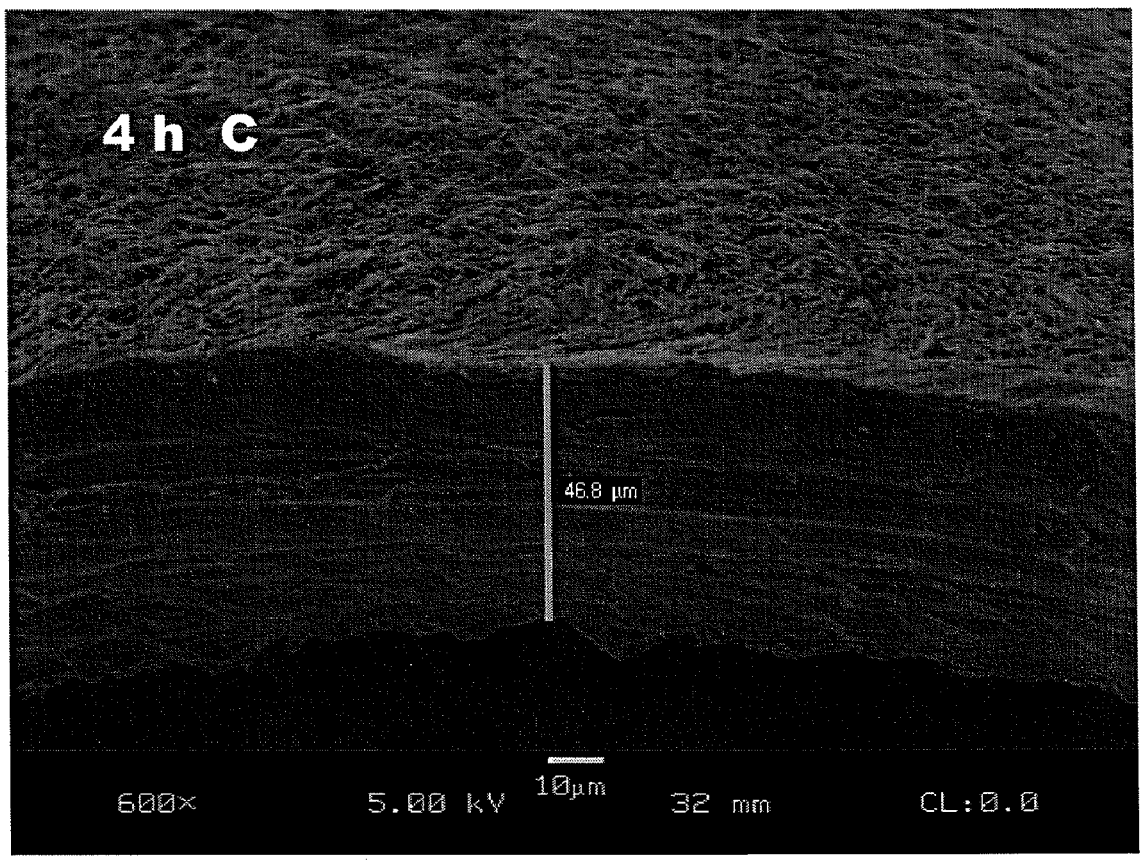
Figure 22D:
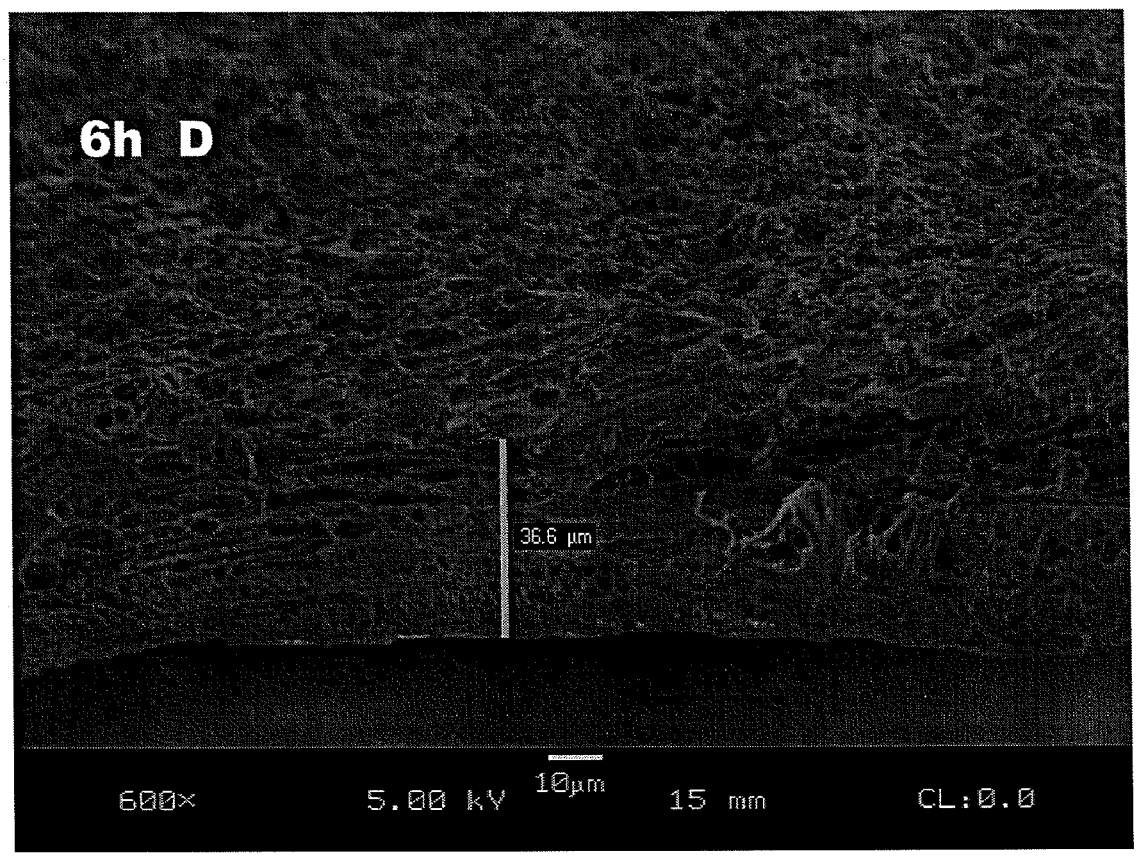
Figure 22E:
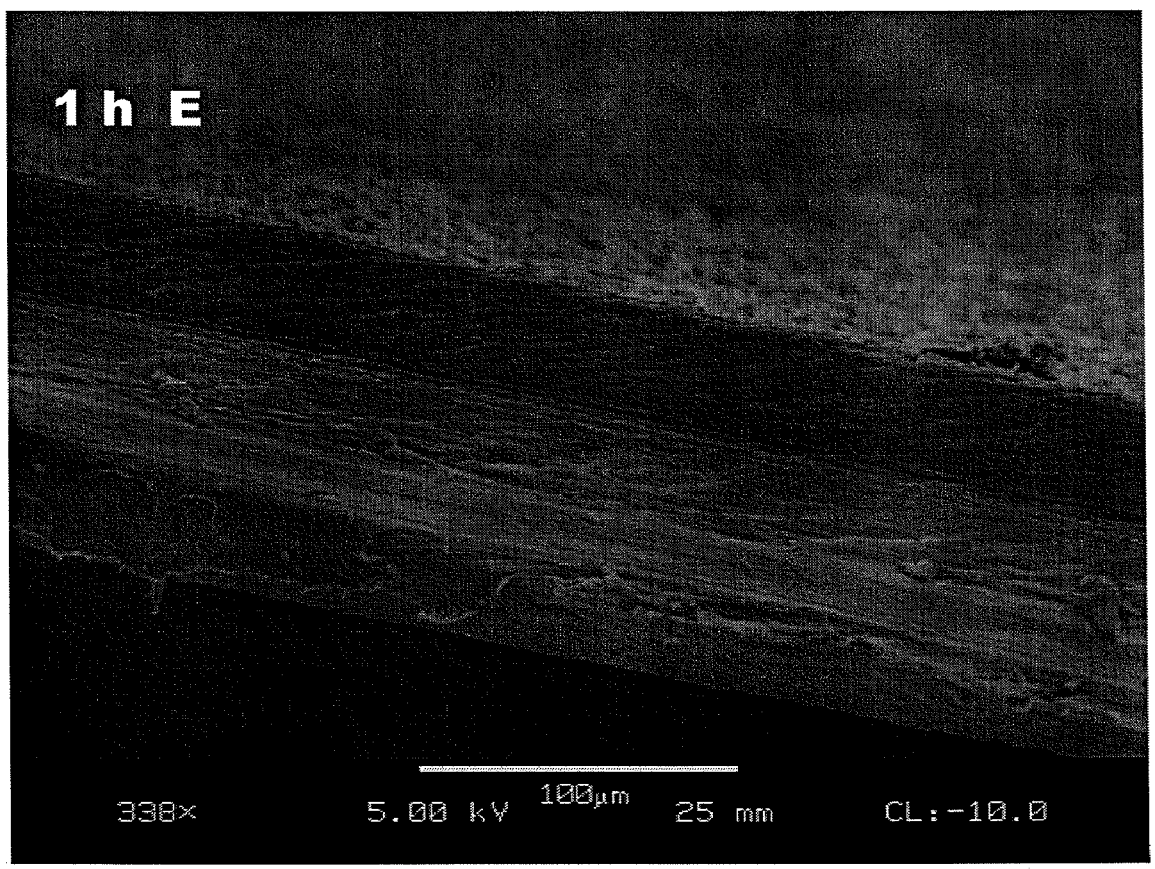
Figure 23:
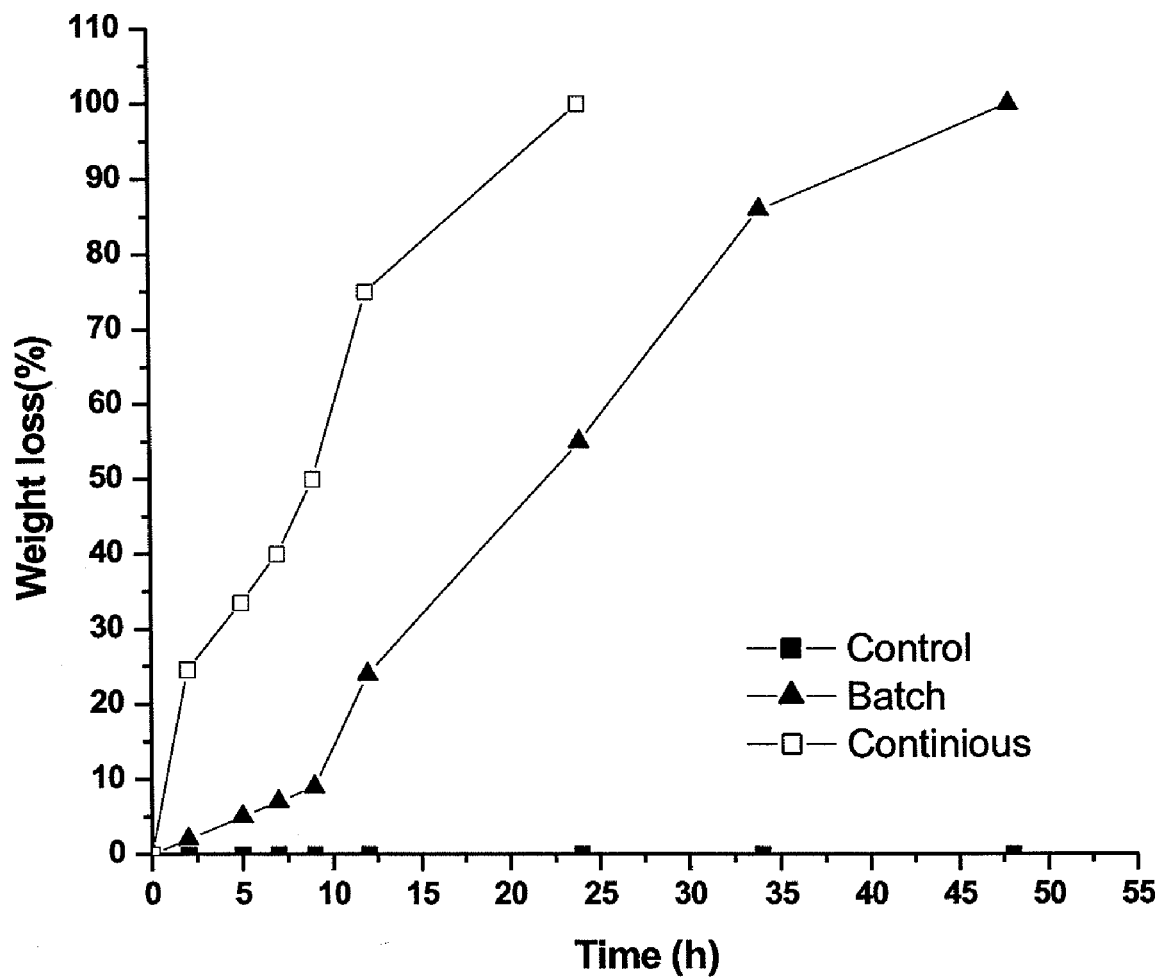
FIG. 23 is a time course of PCL film weight loss as a function of time for incubations carried out with continuous buffer exchange and in the batch mode wherein in both cases, the CALB:AOT complex content in films were 19.4%, w/w.
Figure 24A:
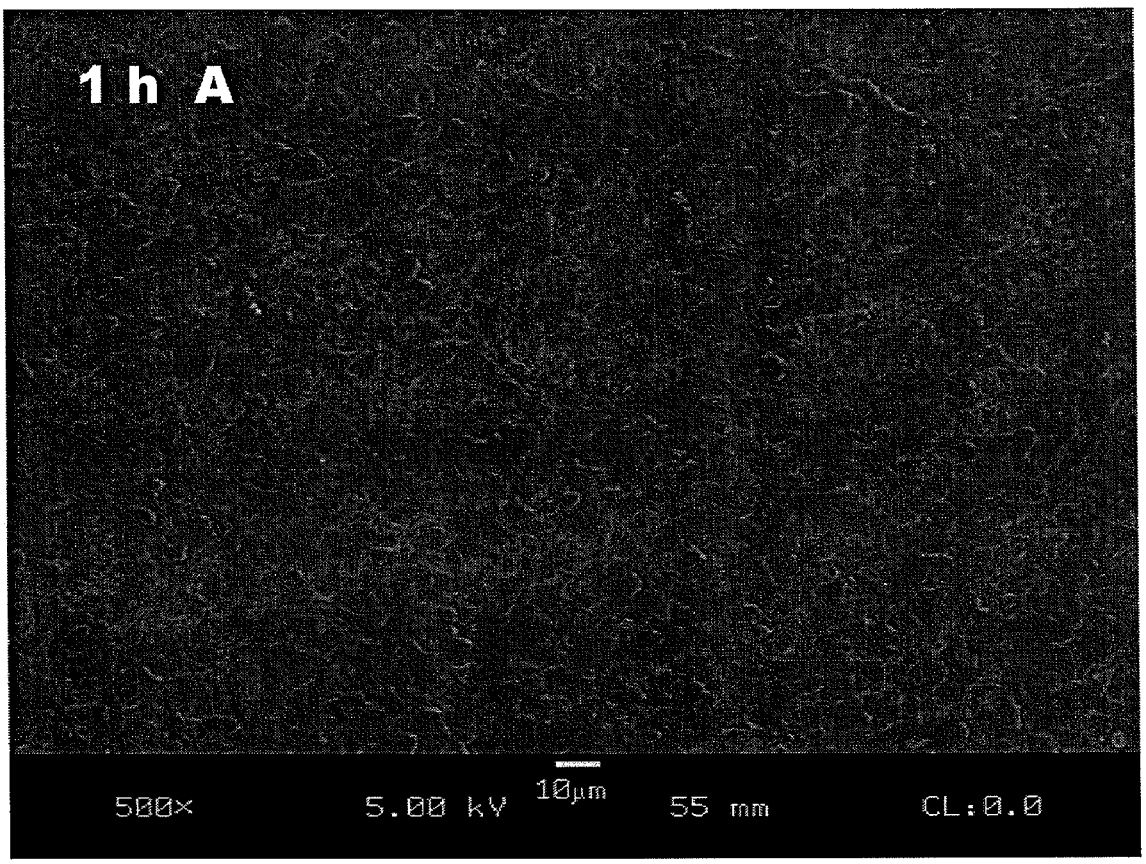
FIG. 24 are representative SEM micrographs of recovered PCL recorded of film cross-sections at 71° in which PCL films were embedded with 19.4% w/w CALB:AOT complex and then incubated in buffer in the continuous buffer removal for 1 h (FIG. 24A), 4 h (FIG. 24B), 8 h (FIG. 24C), 24 h (FIG. 24D), 1 h (FIG. 24E), 8 h (FIG. 24F), and 18 h (FIG. 24G).
Figure 24B:
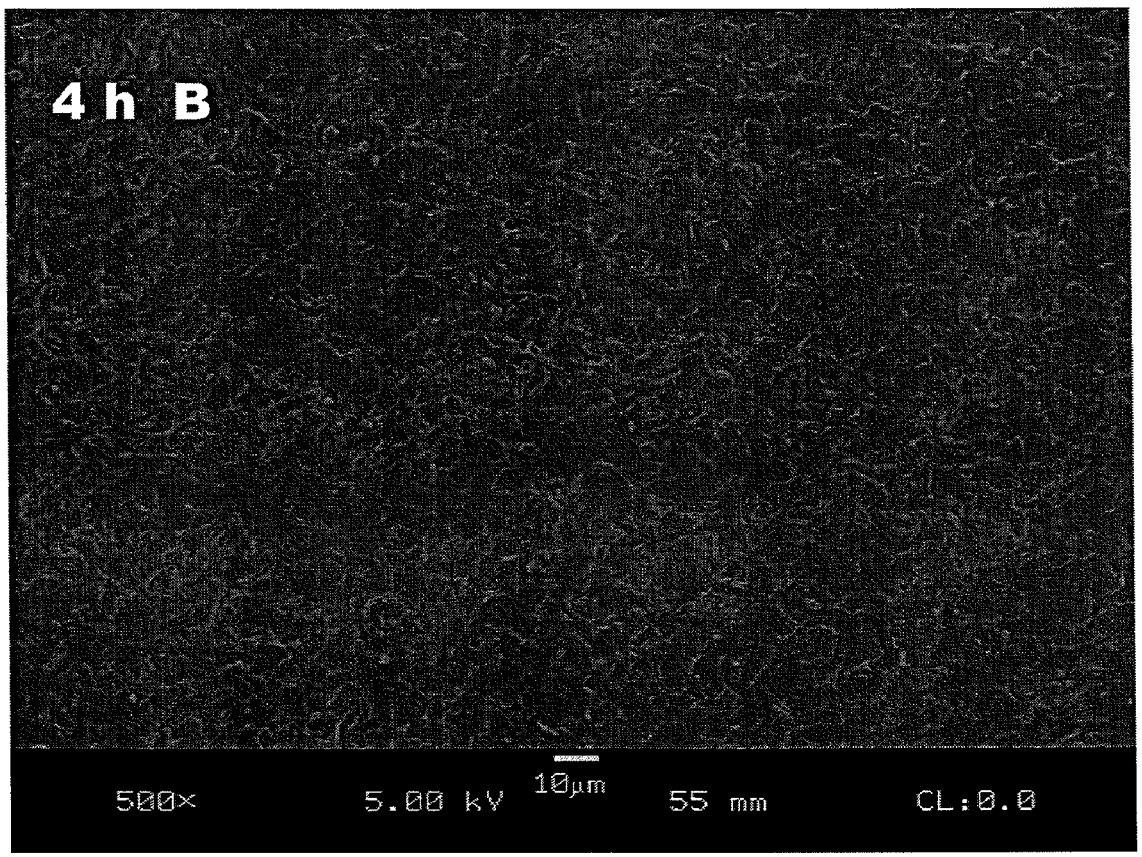
Figure 24C:
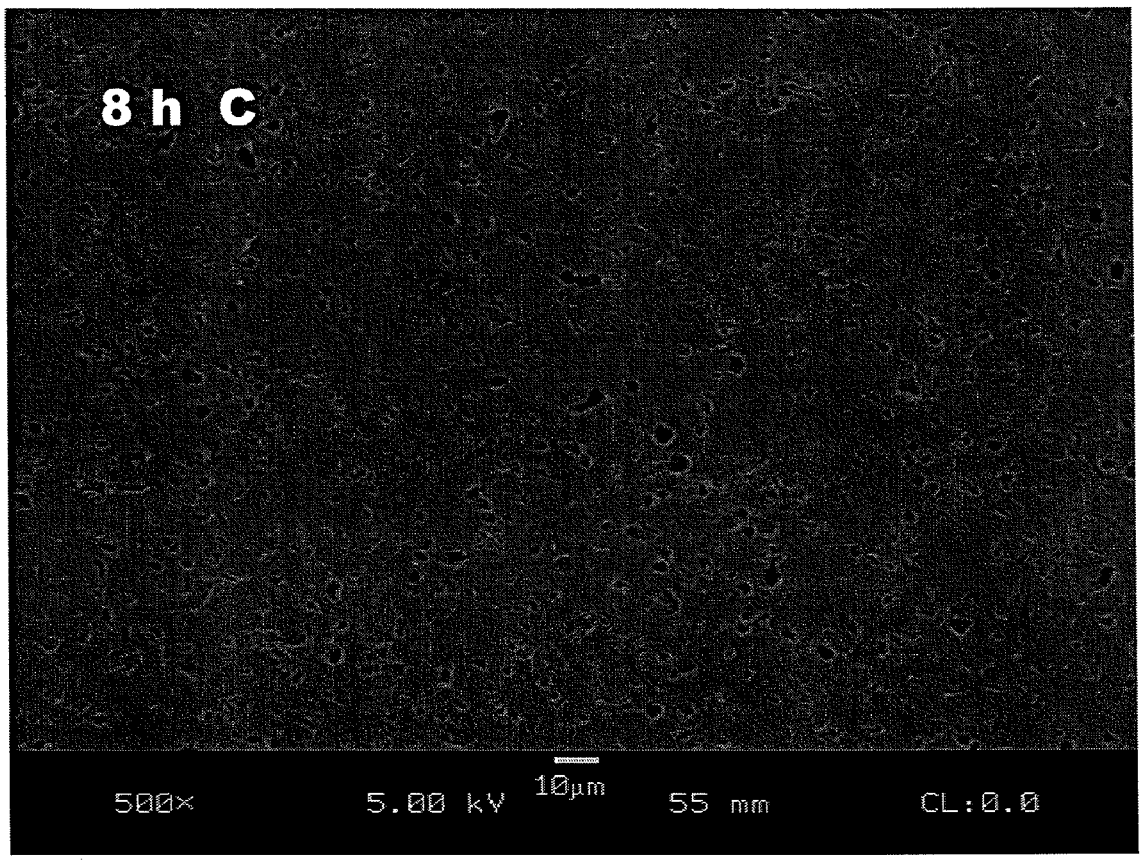
Figure 24D:
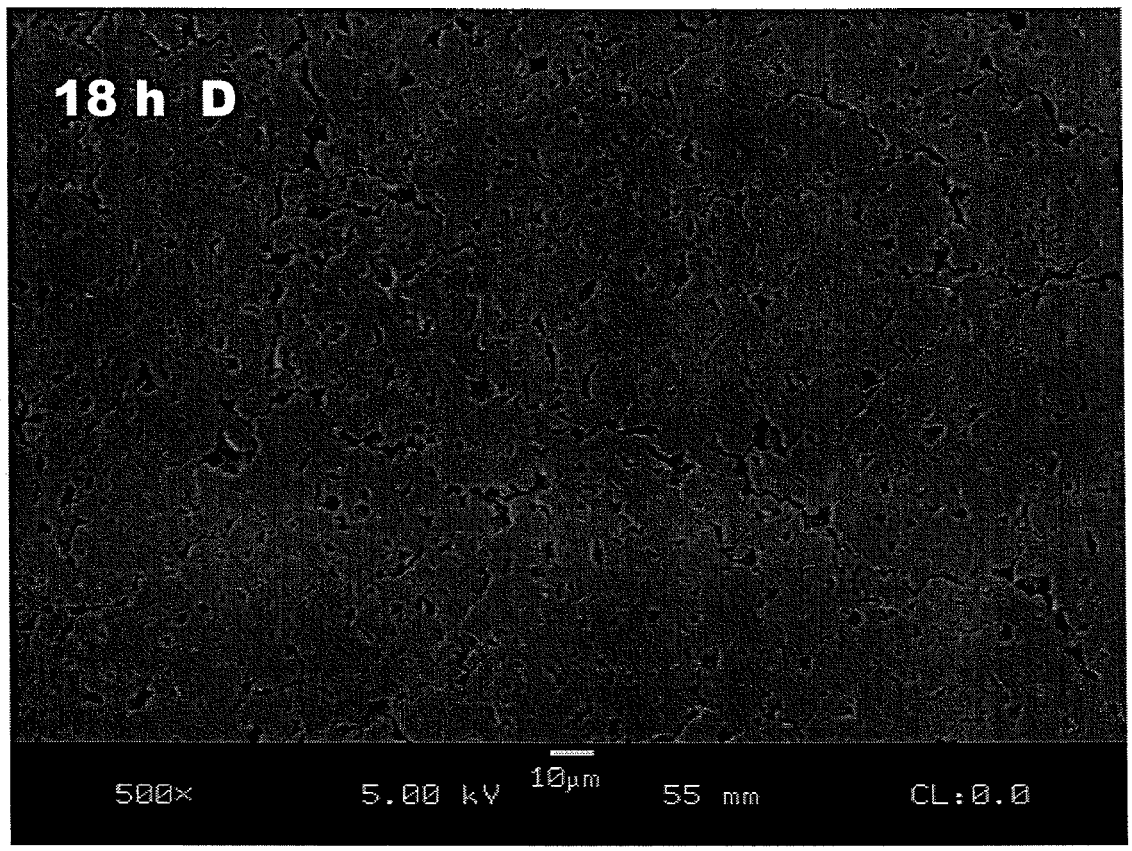
Figure 24E:
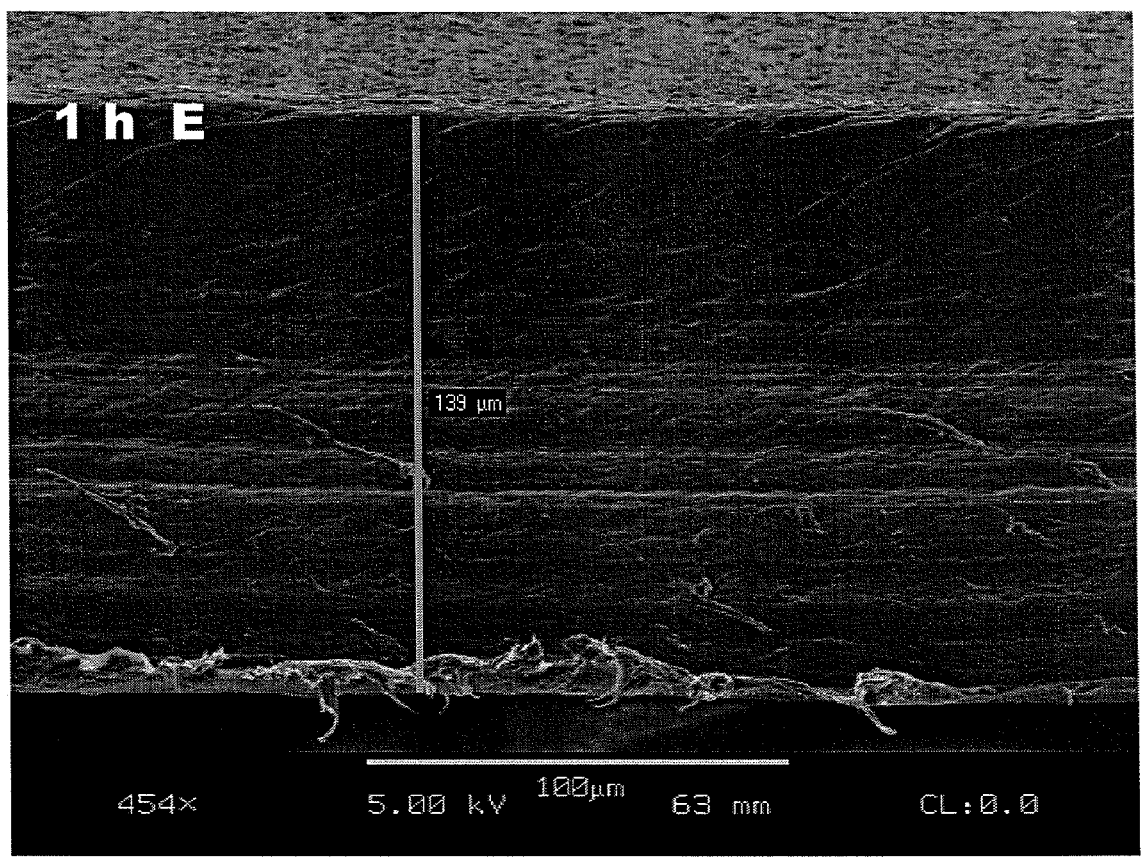
Figure 24F:
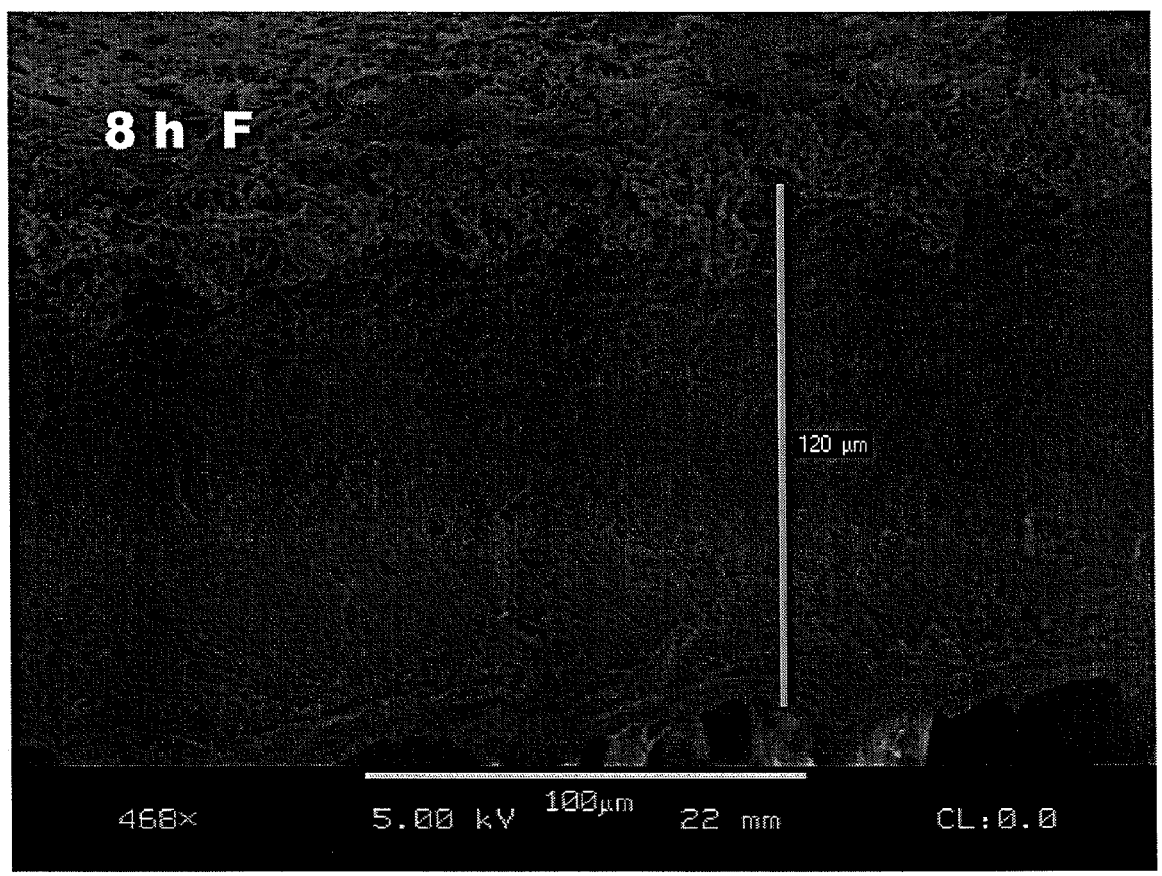
Figure 24G:
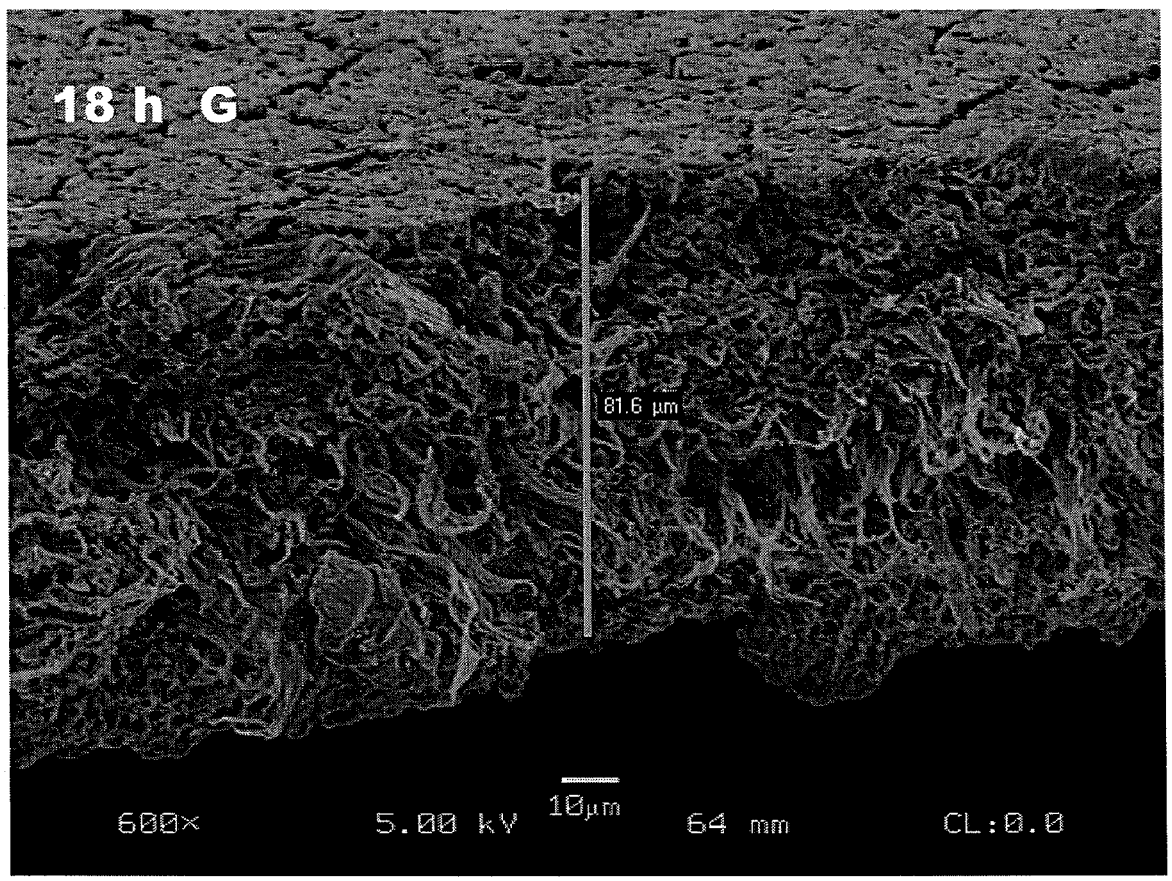

SEM photomicrographs were also recorded through the film cross-section revealing the extent of film degradation below the film surface. FIG. 22D shows a cross-sectional view of a PCL film with 19.4% (w/w) CALB-AOT complexes after 6 h incubation. Throughout the cross-section, holes are observed that correspond to degradation catalyzed by CALB embedded well-below the surface. Thus, sufficient water can diffuse into the bulk to allow CALB throughout the film thickness to be catalytically active in degrading the film from inside-out. In contrast, a cross-sectional view of PCL film degraded by incubation with CALB in the medium without embedding the enzyme shows no degradation in the interior (FIG. 22E). These results show that when enzymes are embedded in PCL films, incubation results in the formation of holes throughout films with concurrent release of CALB into the media.

f. In another set of experiments, degradation studies were performed where the buffer in vials with films was continuously exchanged (see above in Methods). PCL film without embedded CALB was incubated in buffer containing CALB. The enzyme content in the buffer was the same as that used when CALB was embedded in films that are each 2×2 cm film (containing 19.4% CALB-AOT complex). After 2 h the weight loss in the PCL film was 27%. At this time, the pump was started to begin continuous exchange of buffer contents in vials. After an additional 24 h of incubation in the continuous mode, the PCL film did not show further weight loss (i.e. weight loss remained <30%). Another study was performed as above (continuous mode) but where embedded within the PCL film was 19.4% w/w CALB:AOT complex. The film showed complete disintegration to form water-soluble products within only 24 h. In contrast, results above showed that, with 19.4% w/w CALB:AOT complex embedded within films, but performed in the batch mode (without continuous exchange of buffer), complete film disappearance to water soluble products required 48 h. The time-course of film with 19.4% CALB:AOT embedded within films performed in the continuous and batch modes are shown in FIG. 23. The surface and the cross-section properties of the film undergoing continuous buffer removal is shown in FIG. 24.

Figure 25:
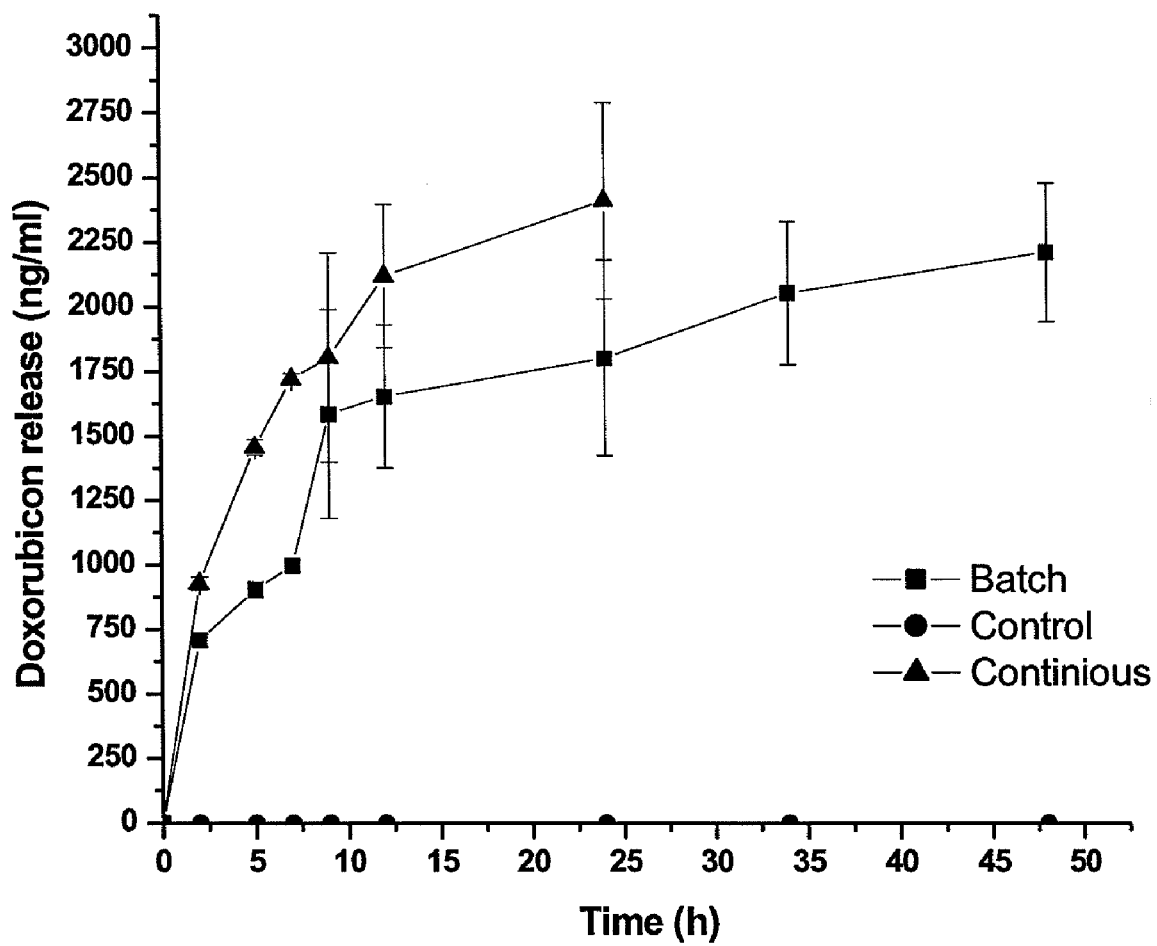
FIG. 25 is a time course of doxorubicin release for incubations carried out with continuous buffer exchange and in the batch mode wherein in both cases, the CALB:AOT complex content in films were 19.4%, w/w.

The results above run in the continuous mode, that compare the degradation of PCL films where CALB is placed only in the incubation medium versus where CALB is embedded within films, demonstrate how important it is to embed the enzyme for continuous film degradation over time, especially when the system has dynamic interchange of fluids.

g. Doxorubicin Release Studies:

Based on the results above, if CALB-AOT complex along with a drug was embedded in the PCL film, this should result in both controlled and accelerated film degradation and drug release. To test this possibility, doxorubicin (DOX) along with CALB-AOT was embedded within the polymer matrix and both film degradation and DOX release was studied. The cumulative DOX release is depicted in FIG. 25. DOX release is accelerated by the presence of embedded CALB-AOT within the film. For batch incubation conditions, release of DOX occurred continuously during the first 9 h. At that point, 45% of DOX had already been released into the medium out of initial 2 µg of DOX in the film. Subsequently, the release between 9 and 48 h occurred at a slower rate. By 48 h, 100% of DOX was successfully released into the buffer. This incubation time also corresponded with complete film disintegration. Doxorubicin release profile from both batch and continuous buffer exchange regiments follows a similar pattern, except that all drug is liberated from the film undergoing continuous buffer exchange in 24 h. This time for complete drug release corresponds with when the film is completely degraded to water-soluble products. No doxorubicin is released in PCL-DOX films without CALB clearly indicating that the drug release corresponds with matrix erosion. Degradable polymers like PCL that degrade by hydrolysis are appealing materials for use in clinical medicine since they disappear after implantation. Degradation is often difficult to control; the above study gives an approach by which the degradation of polymer controlled by an embedded trigger in the polymer matrix leads to drug release.

As disclosed above, FIG. 14 is an illustration of CALB extraction into isooctane and embedding CALB: AOT complex in PCL film.

FIG. 15 is a confocal micrograph displaying the average distribution of the FITC-CALB AOT conjugate within a 100 μm thick PCL film. This figure represents image taken at various depths ranging from 0-48 μm. FIG. 16 is a confocal micrograph displaying within circles the fluorescent regions as Regions of Interest (ROI) for which data was generated for intensity versus depth plots shown in FIG. 17. FIG. 17 shows intensity versus depth profiles of CALB aggregates. The aggregates are marked designating the ROI (Region of Interest) observed (see FIG. 16).

Figure 18:
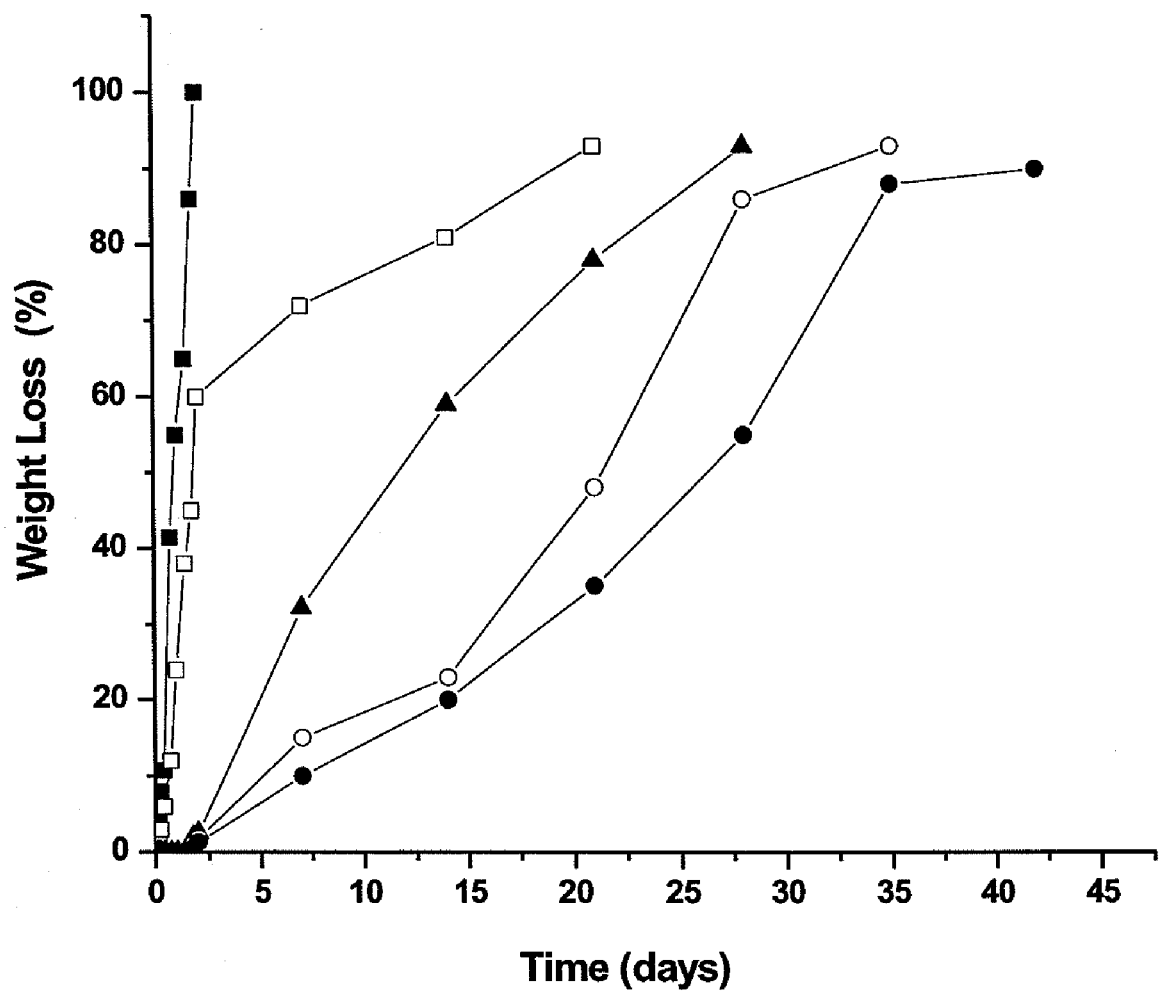
FIG. 18 is a time course of PCL film weight loss as a function of CALB:AOT complex loading in which the weight of CALB:AOT corresponds to its dry weight/per weight of film (w/w), the CALB:AOT complex content in films were 19.4%, w/w (■), 15%, w/w (□), 11.4%, w/w (▲), 5.71%, w/w (○), 3%, w/w (●), and incubations were performed at 200 rpm at 37° C.

FIG. 18 is a time course of PCL film weight loss as a function of CALB:AOT complex loading. The weight of CALB:AOT corresponds to its dry weight/per weight of film (w/w). The CALB:AOT complex content in films were 19.4%, w/w (■), 15%, w/w (□), 11.4%, w/w (▲), 5.71%, w/w (○), 3%, w/w (●). Incubations were performed at 200 rpm at 37° C. FIG. 19 is a molecular weight analysis, determined by gel permeation chromatography, of recovered PCL films that were embedded with 19.4% w/w CaLB:AOT complex and incubated in buffer in batch-mode degradation studies.

FIG. 20 are representative SEM micrographs of recovered PCL films that were embedded with 19.4% w/w CALB:AOT complex and then incubated in buffer in the batch mode for 0 h (A), 30 min (B), 2 h (C), 4 h (D), and 6 h (E). FIG. 21 are representative SEM micrographs of recovered PCL that did not contain embedded enzyme. Instead, an equivalent quantity of CALB used for 19.4% w/w embedded experiments was placed in the incubation medium. Experiments were performed in the batch mode. SEM pictures are displayed from films recovered after incubation periods of 30 mins (A), 60 min (B), and 4 h (C). FIG. 22 are representative SEM micrographs of recovered PCL recorded of film cross-sections at 71°. PCL films were embedded with 19.4% w/w CALB:AOT complex and then incubated in buffer in the batch mode for 0 h (A), 2 h (B), 4 h (C). 6 h (D), and 1 h (E).

FIG. 23 is a time course of PCL film weight loss as a function of time for incubations carried out with continuous buffer exchange and in the batch mode. In both cases, the CALB:AOT complex content in films were 19.4%, w/w.

FIG. 24 are representative SEM micrographs of recovered PCL recorded of film cross-sections at 71°. PCL films were embedded with 19.4% w/w CALB:AOT complex and then incubated in buffer in the continuous buffer removal for 1 h (A), 4 h (B), 8 h (C), 24 h (D), 1 h (E), 8 h (F), and 18 h (G).

FIG. 25 is a time course of doxorubicin release for incubations carried out with continuous buffer exchange and in the batch mode. In both cases, the CALB:AOT complex content in films were 19.4%, w/w.

This detailed description of preferred embodiments has been presented only for illustrative and descriptive purposes, is not intended to be exhaustive, and not intended to limit the scope and spirit of the invention. The embodiments were selected and described to best explain the principles of the invention and its practical applications, and one skilled in the art can recognize that many variations can be made to the invention disclosed herein without departing from the scope and spirit of the invention.

What is claimed is:

1. A method for preparing an enzyme-embedded polymer material comprising the steps of:
   (a) selecting a polymer, wherein the polymer is selected from the group consisting of poly(ε-caprolactone), poly (lactic acid) stereocopolymer, polyesters, polyhydroxyalkanoates, polysaccharides, polycarbonates, polyamides, oligopeptides, pseudopolyamino acids, peptides of higher molecular weight, protein-based materials, polymers prepared from fatty acids with degradable linkages, polyurethanes built from polyols that contain degradable units, mixed linkage polymers that contain various fractions of the above polymer building blocks, and vinyl polymers;
   (b) selecting an enzyme capable of degrading the polymer, wherein the enzyme is selected from the group consisting of lipases, hydrolases, and cutinases;
   (c) incorporating the enzyme selected to degrade the polymer into a polymer matrix formed from the polymer by enzyme-embedded material synthesis, wherein as the polymer matrix is being synthesized, hydrolytic enzymes become associated with the polymer matrix and are incorporated within the polymer matrix; and
   (d) incorporating an active agent into the polymer matrix simultaneously with the polymerization reaction.

2. The method as claimed in claim 1, wherein the polymer matrix is constructed from poly(ε-caprolactone) and the enzyme is a lipase.

3. The method as claimed in claim 2, wherein the enzyme is *Candida antarctica* Lipase B.

4. The method as claimed in claim 1, wherein the polymer matrix is constructed from a poly(lactic acid) stereocopolymer and the enzyme is a serine proteinase.

5. The method as claimed in claim 4, wherein the enzyme is Proteinase K.

6. The method as claimed in claim 1, wherein the polymer is a natural polymer.

7. The method as claimed in claim 1, wherein the polymer is a modified natural polymer.

8. The method as claimed in claim 1, wherein the polymer is a synthetic polymer.

9. The method as claimed in claim 1, wherein the active agent is selected from the group consisting of bioactive agents, pharmaceutical compositions or compounds, nutraceutical compositions or compounds, nutritional components, biologically active components, flavorants, fragrances, detergents, cosmetics, and surface-active compositions.

10. The method as claimed in claim 9, wherein the active agent is a pharmaceutical compound selected from the group consisting of antibiotics, analgesics, vaccines, anti-inflammatory agents, anti-depressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, steroids, compositions to promote growth such as hormones, other growth stimulating agents, and mixtures thereof.

11. The method as claimed in claim 9, wherein the active agent is a nutraceutical component selected from the group consisting of antioxidants, phytochemicals, hormones; vitamins; pantothenate; folic acid; pro-vitamins; minerals; microorganisms; prebiotics; probiotics; trace elements; essential and/or highly unsaturated fatty acids; nutritional supplements; enzymes; pigments; oligopeptides; dipeptides; amino acids; and mixtures thereof.

12. The method as claimed in claim 9, wherein the active agent is a biologically active component selected from the group consisting of herbicides, pesticides, insecticides, rodenticides, fungicides, and mixtures thereof, and hormones, fertilizers, other growth stimulating agents, and mixtures thereof.

13. A method for preparing an enzyme-embedded polymer material comprising the steps of:
 (a) incorporating a lipase into a polymer matrix formed from a polymer selected from the group consisting of poly($\epsilon$-caprolactone) and poly(lactic acid) by enzyme-embedded material synthesis, wherein as the polymer matrix is being synthesized, hydrolytic enzymes become associated with the polymer matrix and are incorporated within the polymer matrix; and
 (b) incorporating an active agent into the polymer matrix simultaneously with the polymerization reaction.

14. The method as claimed in claim 13, wherein the enzyme is *Candida antartica* Lipase B.

15. The method as claimed in claim 13, wherein the active agent is selected from the group consisting of bioactive agents, pharmaceutical compositions or compounds, nutraceutical compositions or compounds, nutritional components, biologically active components, flavorants, fragrances, detergents, cosmetics, and surface-active compositions.

16. A method for preparing an enzyme-embedded polymer material comprising the steps of:
 (a) selecting a polymer as a substrate, wherein the polymer is poly($\epsilon$-caprolactone);
 (b) selecting an enzyme from the group consisting of lipases, hydrolases, and cutinases that are capable of degrading the polymer;
 (c) mixing the enzyme with the polymer to prepare an enzyme-embedded polymer matrix, wherein the enzyme-embedded polymer matrix degrades at a rate dependent on the selected enzyme, the content of the selected enzyme within the enzyme-embedded polymer matrix, and the amount of water present; and
 (d) incorporating an active agent into the polymer matrix simultaneously with the formation of the polymer matrix.

17. The method as claimed in claim 16, wherein the enzyme is a lipase.

18. The method as claimed in claim 17, wherein the enzyme is *Candida antarctica* Lipase B.

19. The method as claimed in claim 16, wherein the active agent is a pharmaceutical compound selected from the group consisting of antibiotics, analgesics, vaccines, anti-inflammatory agents, anti-depressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, steroids, compositions to promote growth such as hormones, other growth stimulating agents, and mixtures thereof.

20. The method as claimed in claim 16, wherein the active agent is a nutraceutical component selected from the group consisting of antioxidants, phytochemicals, hormones; vitamins; pantothenate; folic acid; pro-vitamins; minerals; microorganisms; prebiotics; probiotics; trace elements; essential and/or highly unsaturated fatty acids; nutritional supplements; enzymes; pigments; oligopeptides; dipeptides; amino acids; and mixtures thereof.

21. The method as claimed in claim 16, wherein the active agent is a biologically active component selected from the group consisting of herbicides, pesticides, insecticides, rodenticides, fungicides, and mixtures thereof, and hormones, fertilizers, other growth stimulating agents, and mixtures thereof.

* * * * *